United States Patent
Xu et al.

(10) Patent No.: US 9,590,190 B2
(45) Date of Patent: Mar. 7, 2017

(54) TERMINALLY ACTIVATED DELAYED FLUORESCENCE MATERIAL, A METHOD OF SYNTHESIZING THE SAME AND AN OLED DEVICE USING THE SAME

(71) Applicant: Shenzhen China Star Optoelectronics Technology Co., Ltd., Shenzhen, Guangdong (CN)

(72) Inventors: Shidang Xu, Guangdong (CN); Zhenguo Chi, Guangdong (CN); Yi Zhang, Guangdong (CN); Jiarui Xu, Guangdong (CN); Yifan Wang, Guangdong (CN); Qinghua Zou, Guangdong (CN)

(73) Assignee: Shenzhen China Star Optoelectronics Technology Co., Ltd, Shenzhen, Guangdong (CN)

( * ) Notice: Subject to any disclaimer, the term of this patent is extended or adjusted under 35 U.S.C. 154(b) by 437 days.

(21) Appl. No.: 14/347,618

(22) PCT Filed: Jan. 13, 2014

(86) PCT No.: PCT/CN2014/070505
§ 371 (c)(1),
(2) Date: Mar. 26, 2014

(87) PCT Pub. No.: WO2015/096226
PCT Pub. Date: Jul. 2, 2015

(65) Prior Publication Data
US 2015/0270494 A1    Sep. 24, 2015

(30) Foreign Application Priority Data
Dec. 26, 2013 (CN) .......................... 2013 1 0733731

(51) Int. Cl.
*H01L 51/54* (2006.01)
*C09K 11/06* (2006.01)
(Continued)

(52) U.S. Cl.
CPC ........ *H01L 51/0072* (2013.01); *C07D 209/86* (2013.01); *C07D 279/22* (2013.01); *C07D 417/14* (2013.01); *C09K 11/06* (2013.01); *H01L 51/0071* (2013.01); *C09K 2211/1007* (2013.01); *C09K 2211/1011* (2013.01); *C09K 2211/1037* (2013.01); *C09K 2211/1066* (2013.01); *H01L 51/5012* (2013.01); *H01L 51/5068* (2013.01);
(Continued)

(58) Field of Classification Search
CPC .. C07D 209/82; C07D 209/86; C07D 279/00; C07D 279/14; C07D 279/22; C07D 417/00; C07D 417/14; C09K 11/06; C09K 2211/10; C09K 2211/1003; C09K 2211/1007; C09K 2211/1014; C09K 2211/1018; C09K 2211/1029; C09K 2211/1037; C09K 2211/1044; C09K 2211/1051; C09K 2211/1059; C09K 2211/1066; H01L 51/0032; H01L 51/005; H01L 51/0071; H01L 51/0072; H01L 51/50; H01L 51/5012; H01L 51/5056; H01L 51/5072; H01L 51/5084; H01L 51/5234
USPC ....... 428/690, 691, 917, 411.4, 336; 427/58, 427/66; 313/500–512; 257/40, 88–14, 257/E51.001–E51.052; 252/301.16–301.35
See application file for complete search history.

(56) References Cited

U.S. PATENT DOCUMENTS

| | | | |
|---|---|---|---|
| 9,328,097 B2 * | 5/2016 | Xu ....................... | C07D 403/12 |
| 2015/0141642 A1 * | 5/2015 | Adachi ................ | C07C 317/36 |
| | | | 544/102 |

FOREIGN PATENT DOCUMENTS

| | | |
|---|---|---|
| CN | 103483332 A | 1/2014 |
| JP | 2004220931 A | 8/2004 |

(Continued)

OTHER PUBLICATIONS

Zhang et al. J. Am. Chem. Soc. 2012, 134, 14706-14709. Date of publication: Aug. 29, 2012.*

(Continued)

*Primary Examiner* — Andrew K Bohaty
(74) *Attorney, Agent, or Firm* — Andrew C. Cheng

(57) ABSTRACT

The present invention provides a thermally activated delayed fluorescence material, a method of synthesizing the same and an OLED device using the same. The thermally activated delayed fluorescence material includes a structure formula 1 as

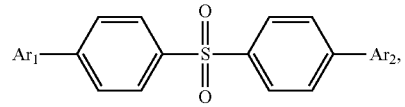

wherein the group Ar1 is identical to or different from the group Ar2, and the group Ar1 and the group Ar2 are consisted of carbazole and/or phenothiazine. The thermally activated delayed fluorescence material has a higher glass transition temperature, high thermal stability and excellent luminous efficiency. The method of synthesizing the same has simplified steps, easily purified product, high yield, and luminous and thermal properties of the product can be adjusted by connecting to differentiated functional groups. The OLED device using the same has a light emitting layer of high fluorescence efficiency and long-term stability, so that luminous efficiency and service life of the OLED device can meet practical demand.

7 Claims, 2 Drawing Sheets

(51) Int. Cl.
  *H01L 51/00*    (2006.01)
  *C07D 209/86*   (2006.01)
  *C07D 417/14*   (2006.01)
  *C07D 279/22*   (2006.01)
  *H01L 51/50*    (2006.01)
  *H01L 51/52*    (2006.01)

(52) U.S. Cl.
  CPC ...... *H01L 51/5084* (2013.01); *H01L 51/5234* (2013.01)

(56) References Cited

FOREIGN PATENT DOCUMENTS

TW            201343874 A    11/2013
WO    WO2013161437 A1   10/2013

OTHER PUBLICATIONS

Kimoto et al. Macromolecules 2004, 37, 5531-5537. Year of publication: 2004.*

\* cited by examiner

TERMINALLY ACTIVATED DELAYED FLUORESCENCE MATERIAL, A METHOD OF SYNTHESIZING THE SAME AND AN OLED DEVICE USING THE SAME

FIELD OF THE INVENTION

The present invention relates to organic light emitting techniques, and more particularly relates to a thermally activated delayed fluorescence material, a method of synthesizing the same and an OLED device using the same.

BACKGROUND OF THE INVENTION

Due to great potential application to flexible display devices etc., the organic light emitting diode (OLED) device is attached great importance by the scientific community and display industry in recent years, and it is one of the hot spots of current research and development.

However, the OLED device technology is currently experiencing a bottleneck in the development process; a main issue is that light emitting efficiency and lifetime of the OLED device cannot meet practical demand so as to greatly limit the development of the OLED technology. Factors of affecting the luminous efficiency and service life of the OLED device are multifaceted, but the fluorescence efficiency and stability of the light emitting material directly affect the performance of the OLED device. A first generation light emitting material that converts electrical energy into light based on singlet state exciton only has 25% theoretical conversion efficiency, and the conversion efficiency thereof cannot be further increased. A second generation light emitting material (i.e. phosphorescent material) that converts electrical energy into light based on triplet state exciton has theoretical conversion efficiency up to 100%; however, the phosphorescent material has some drawbacks, such as blue phosphorescence of poor efficiency and short lifetime, unable to be resolved.

In 2012, professor Adachi at Kyushu University in Japan found a new material of thermally activated delayed fluorescence (TADF) based on triplet-singlet state transition, and TADF has conversion efficiency close to 100% and blue phosphorescence without the drawbacks as the phosphorescent material. Such new materials as TADF are known as third generation efficient light emitting material of OLED. In comparison with the phosphorescent material, the new material can provide high luminous efficiency without using the rare metals of high cost. Therefore, the new material has features of high luminous efficiency and low fabrication cost. It is estimated that fabrication cost of an OLED device using the new material is less than one tenth cost of an OLED using the conventional material such as the phosphorescent material.

The new material has just been discovered and immediately caused great concern to scientific community and display industry related thereto. However, the new material is very scarce, and the theory thereof is still imperfect, so the new material needs further research and development by researchers. Additionally, based on report, TADF has relatively low glass transition temperature and poor thermal stability.

SUMMARY OF THE INVENTION

In accordance with an aspect, the present invention provides a thermally activated delayed fluorescence material. The thermally activated delayed fluorescence material combines multi carbazole and/or phenothiazine of high thermal stability so as to have a higher glass transition temperature, high thermal stability and excellent luminous efficiency.

In accordance with another aspect, the present invention provides a method of synthesizing the thermally activated delayed fluorescence material. The method of synthesizing the same has simplified steps, easily purified product, high yield, and luminous and thermal properties of the product can be adjusted by connecting to differentiated functional groups.

In accordance with another aspect, the present invention provides an OLED device using the thermally activated delayed fluorescence material. The OLED device using the same has a light emitting layer of high fluorescence efficiency and long-term stability, so that luminous efficiency and service life of the OLED device can meet practical demand.

For the above aspects, the present invention provides a thermally activated delayed fluorescence material including a structure formula 1 as

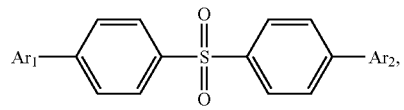

wherein the group Ar1 is identical to or different from the group Ar2, and the group Ar1 and the group Ar2 are consisted of carbazole and/or phenothiazine.

In an embodiment, the group Ar1 and the group Ar2 are selected from the following structure formulas:

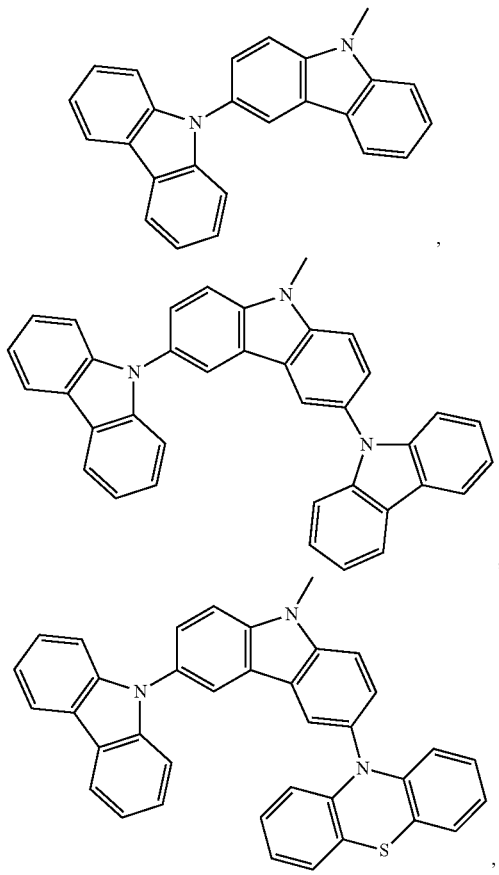

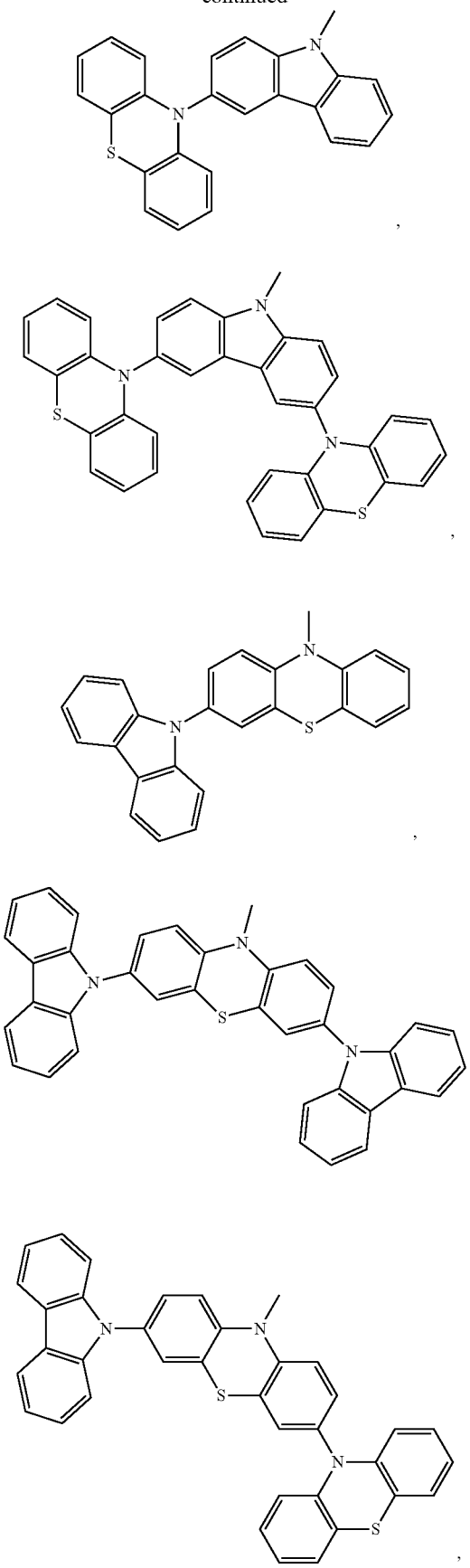

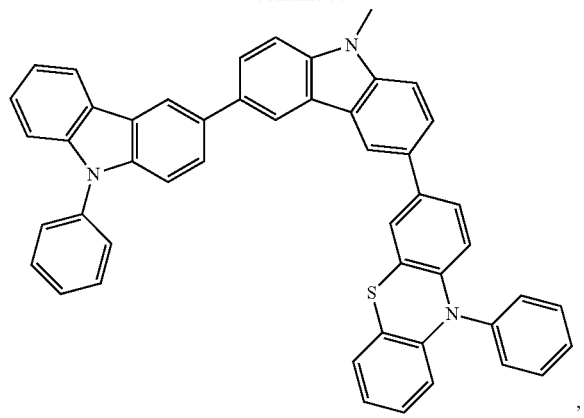
,
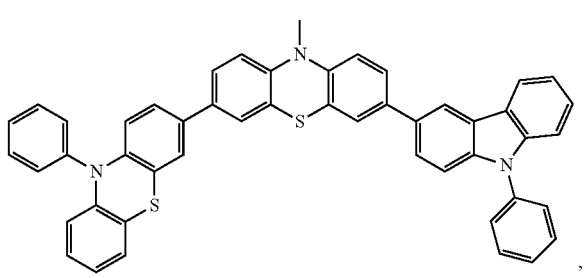
,
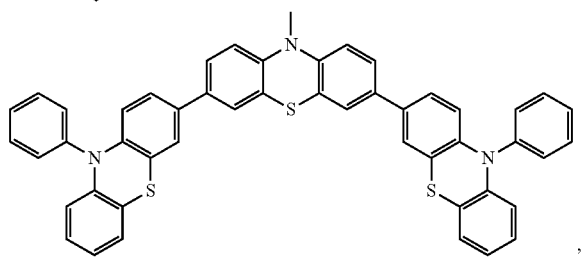
,
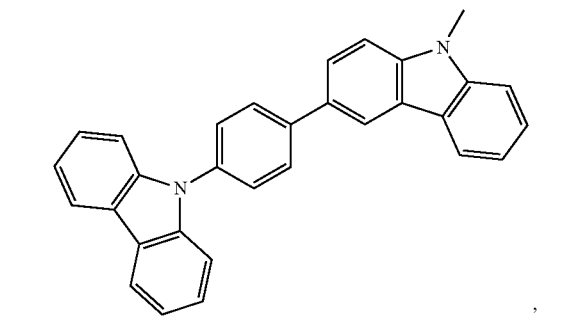
,
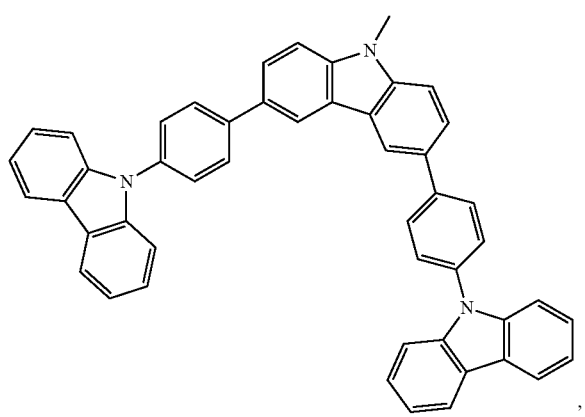
,

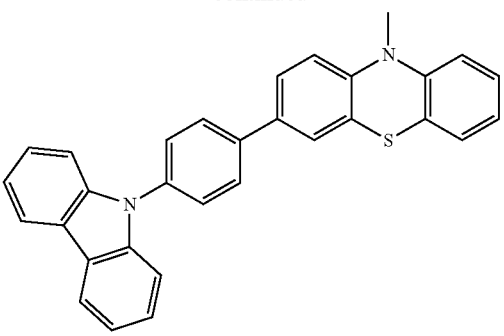
,
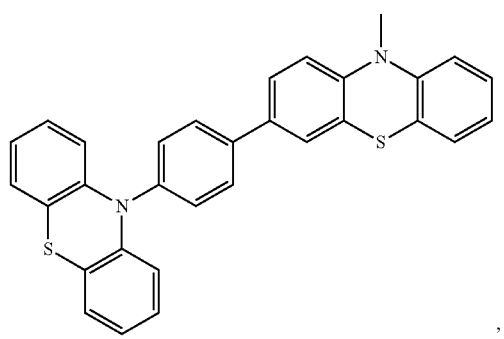
,
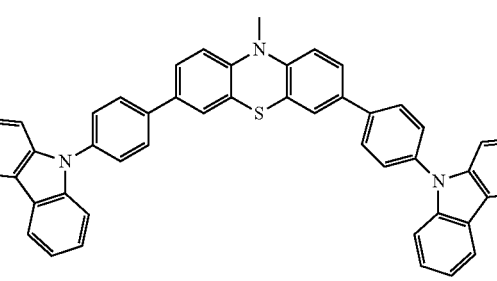
,
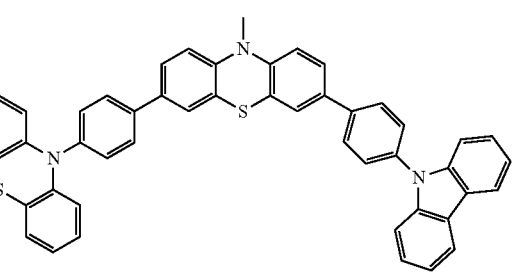
,
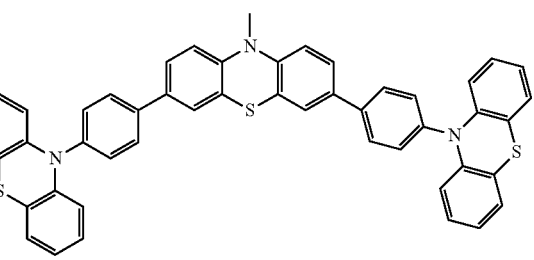
or
.

For the above aspects, the present invention provides a method of synthesizing the thermally activated delayed fluorescence material including steps as follows. Step 1, carbazole and/or phenothiazine units are provided, and one of the carbazole and/or phenothiazine units is coupled to the other carbazole or phenothiazine units by performing a coupling reaction to form a first intermediate. Step 2, 4-fluorophenyl sulfone is provided and reacts with the first intermediate formed in Step 1 to form a product that is a thermally activated delayed fluorescence material including a structure formula 1 as

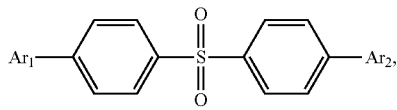

wherein the group Ar1 is identical to or different from the group Ar2, and the group Ar1 and the group Ar2 are consisted of carbazole and/or phenothiazine.

In an embodiment, performing the coupling reaction includes sub-steps as follows. Firstly, the carbazole and/or phenothiazine unit reacts with acetic anhydride to form N-acetyl carbazole of position 3 or positions 3, 6 substituted, or phenothiazine of position 3 or positions 3, 7 substituted. Then, an iodination of the N-acetyl carbazole of position 3 or positions 3, 6 substituted, or the phenothiazine of position 3 or positions 3, 7 substituted is performed to form a second intermediate including iodo carbazole, diido carbazole, iodo phenothiazine or diiodo phenothiazine protected with acetyl group. Then, the second intermediate reacts with the other carbazole or phenothiazine unit, and a deacetylation is performed to form the first intermediate.

In an embodiment, the group Ar1 and the group Ar2 are selected from the following structure formulas:

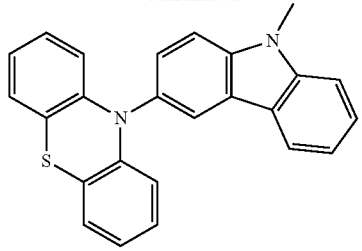

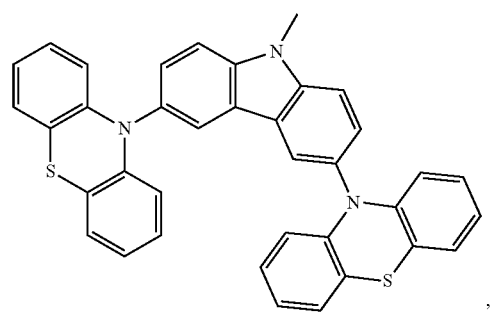

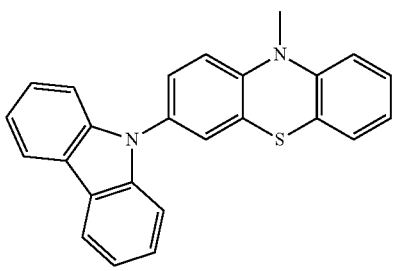

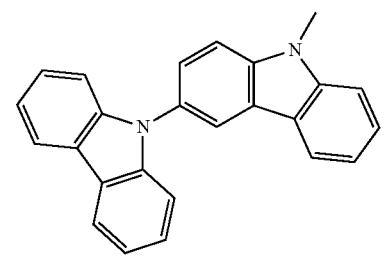

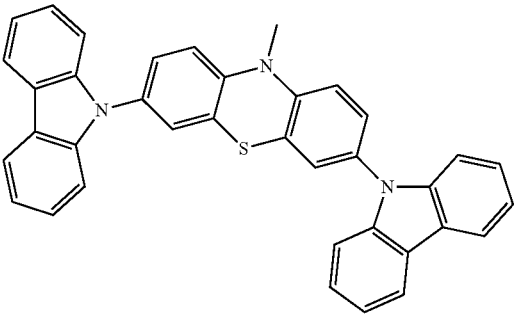

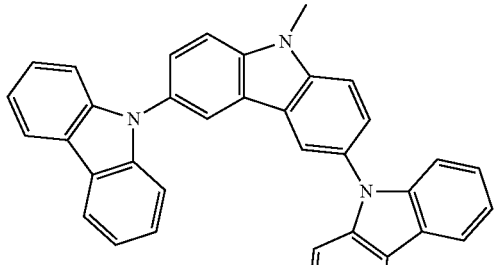

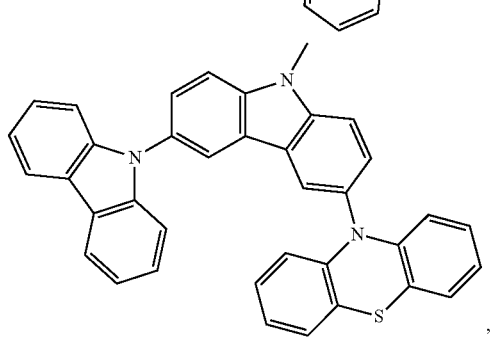

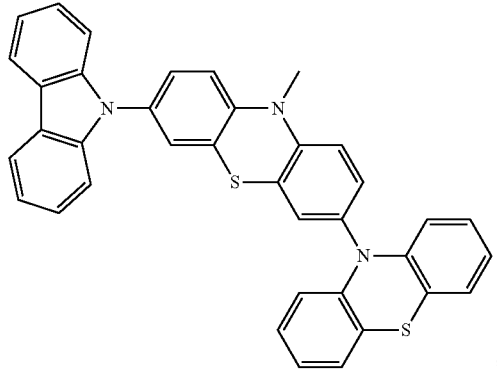

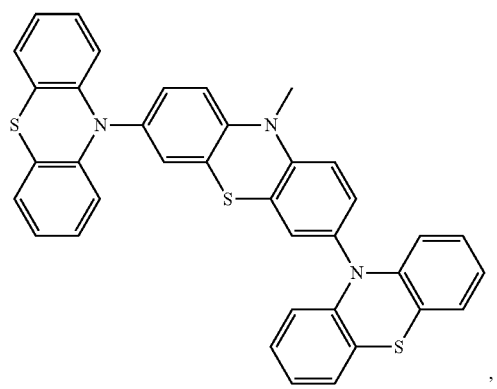
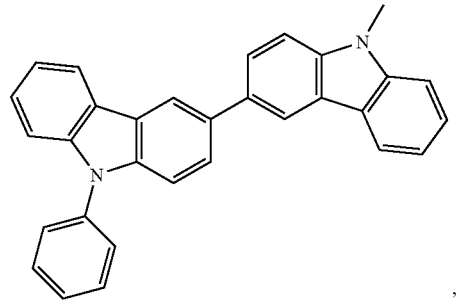
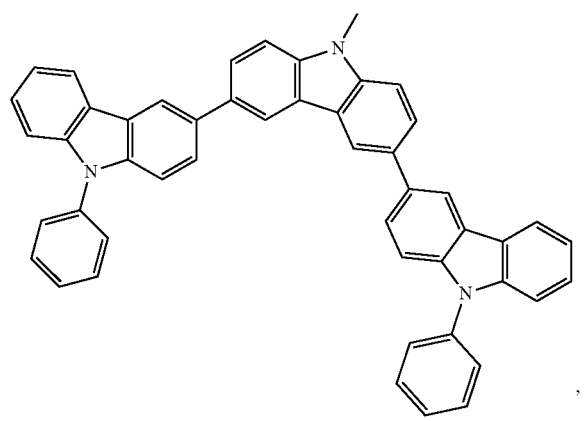
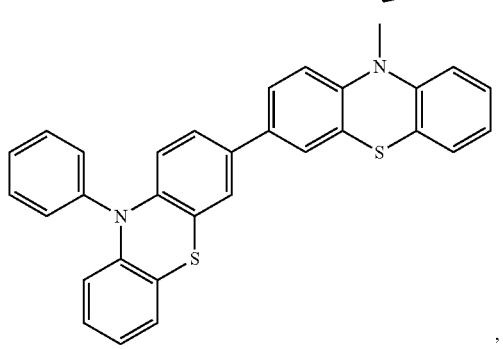
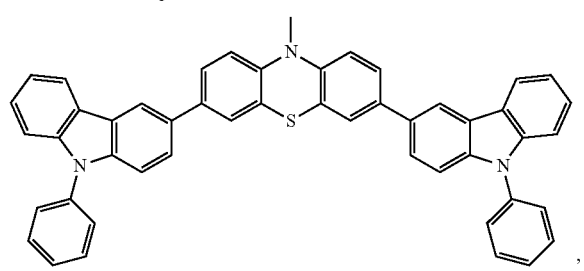
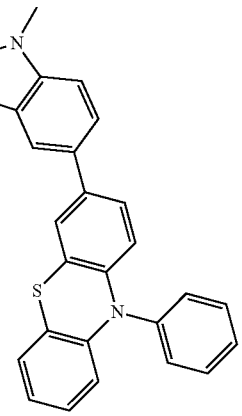
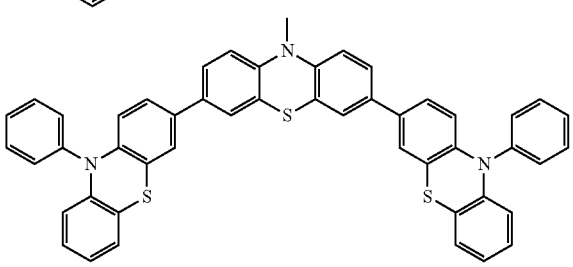
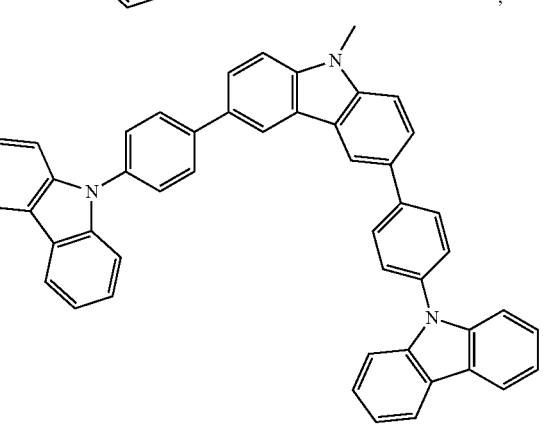

-continued

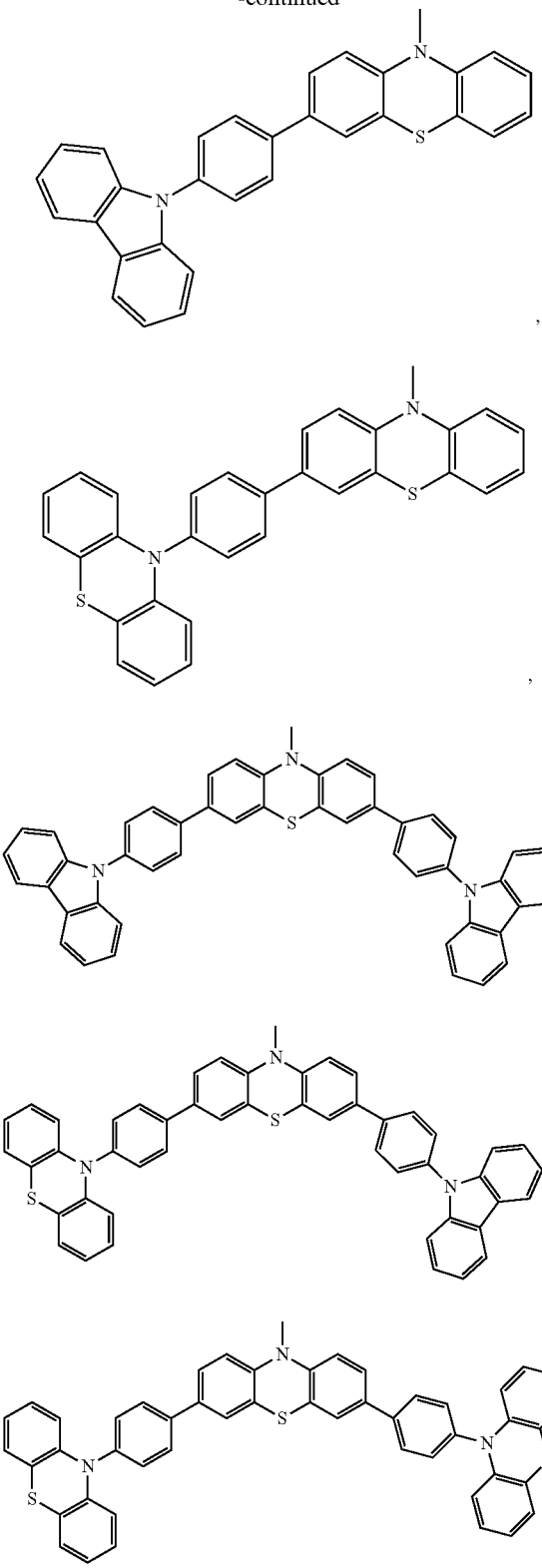

halogeno phenothiazine is reacted with the 4-fluorophenyl sulfone to form a third intermediate. Step 12, substituted or unsubstituted carbazole boronic acid or phenothiazine boronic acid is provided, and the substituted or unsubstituted carbazole boronic acid or phenothiazine boronic acid reacts with the third intermediate formed in Step 11 to form a thermally activated delayed fluorescence material including a structure formula 1 as

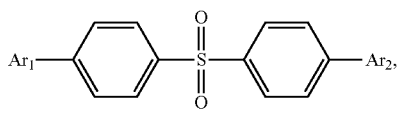

wherein the group Ar1 is identical to or different from the group Ar2, and the group Ar1 and the group Ar2 are consisted of carbazole and/or phenothiazine.

In an embodiment, the halgeno carbazole or halogeno phenothiazine is a monohalogenated or dihalogenated compound, and the halgeno carbazole or halogeno phenothiazine is a bromo compound.

In an embodiment, the halgeno carbazole is 3-bromo carbazole or 3,6-dibromo carbazole, and the halogeno phenothiazine is 3-bromo phenothizzine or 3,7-dibromo phenothiazine.

In an embodiment, the group Ar1 and the group Ar2 are selected from the following structure formulas:

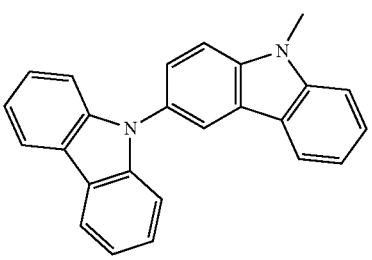

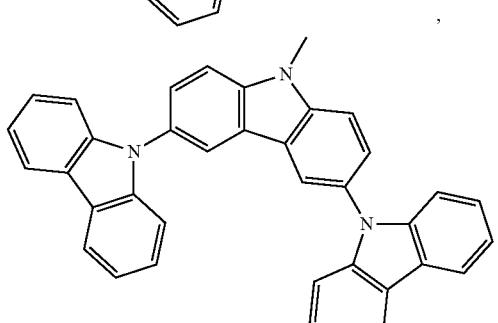

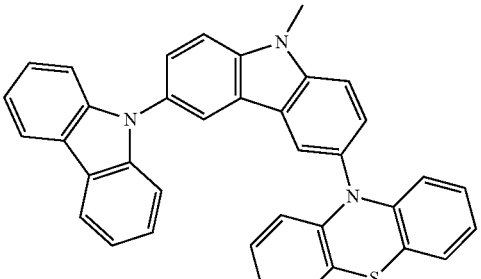

For the above aspect, the present invention provides a method of synthesizing the thermally activated delayed fluorescence material including steps as follows. Step 11, halgeno carbazole or halogeno phenothiazine and 4-fluorophenyl sulfone are provided, and the halgeno carbazole or

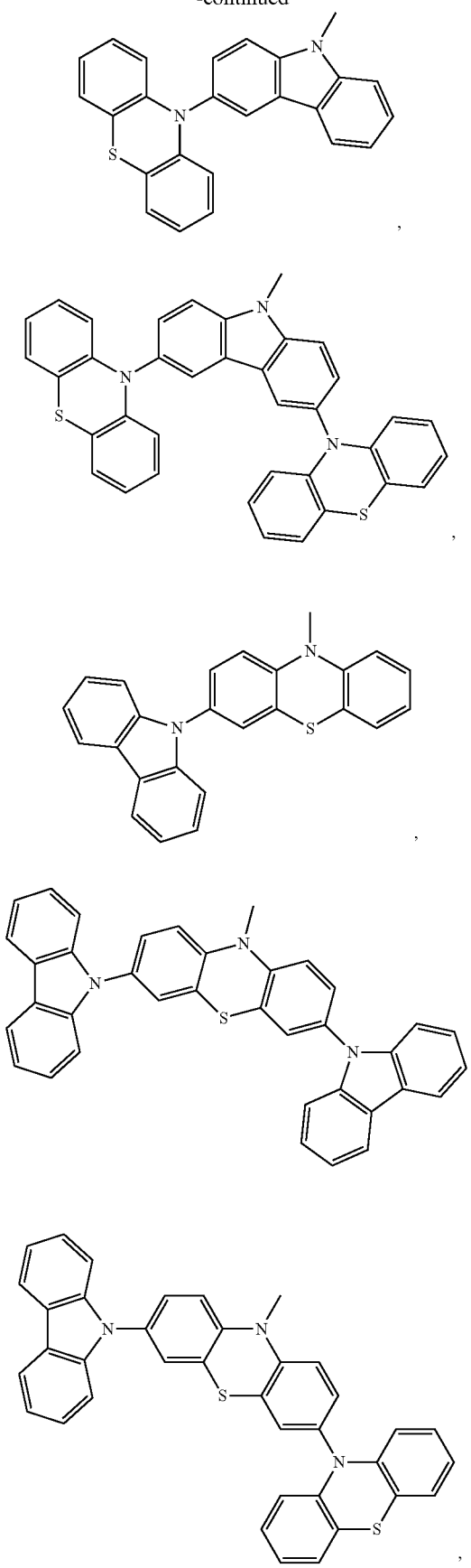

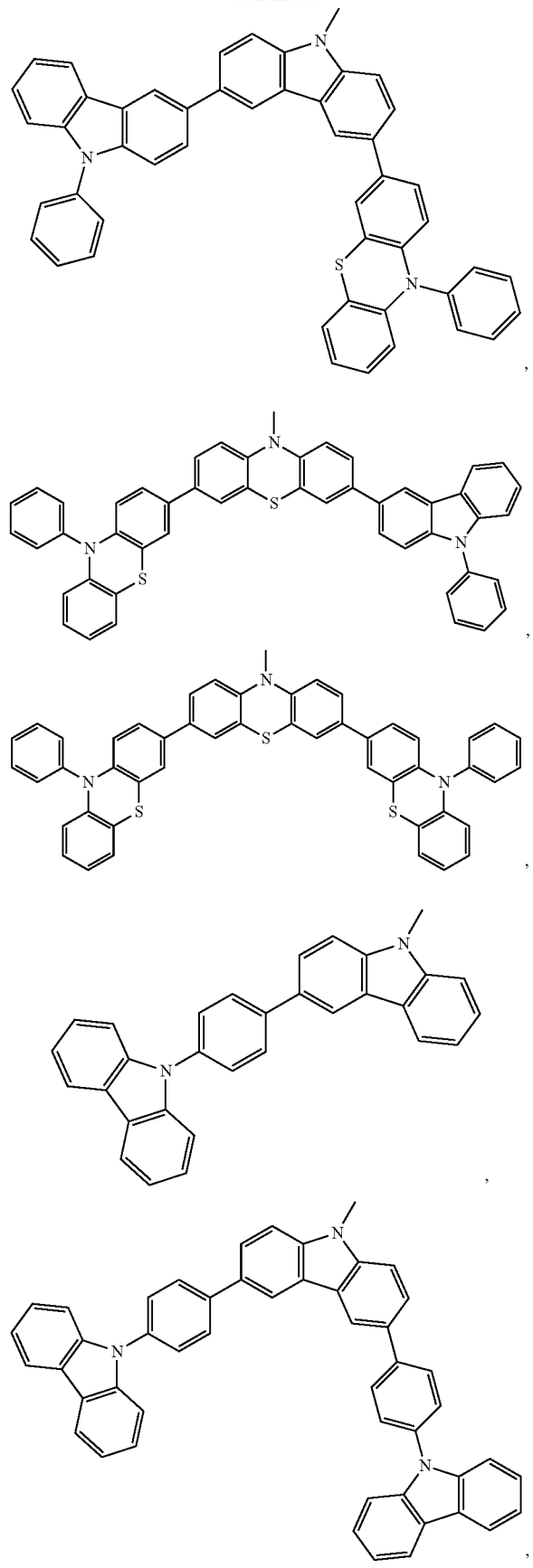

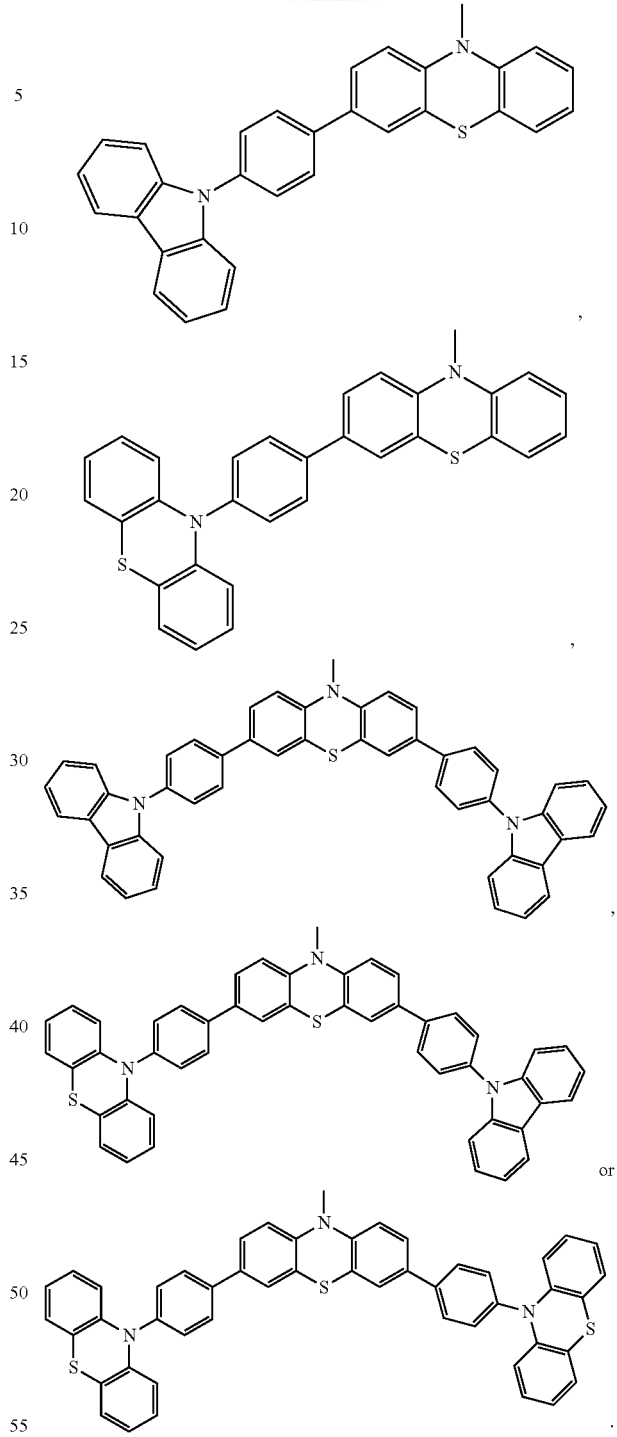

For the above aspect, the present invention provides an OLED device using the thermally activated delayed fluorescence. The OLED device using the same includes a substrate, a transparent conductive layer, a hole transport layer, a light emitting layer, an electron transport layer and a metal layer. The transparent conductive layer is formed on the substrate. The hole transport layer is formed on the transparent conductive layer. The light emitting layer is formed on the hole transport layer. The electron transport layer is formed on the light emitting layer. The metal layer is formed on the electron transport layer. The light emitting layer includes a thermally activated delayed fluorescence material including a structure formula 1 as

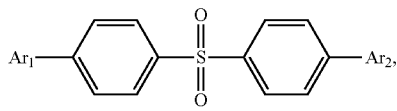

wherein the group Ar1 is identical to or different from the group Ar2, and the group Ar1 and the group Ar2 are consisted of carbazole and/or phenothiazine.

According to the present invention, the thermally activated delayed fluorescence material combines multi carbazole and/or phenothiazine of high thermal stability so as to have a higher glass transition temperature, high thermal stability and excellent luminous efficiency. The method of synthesizing the same has simplified steps, easily purified product, high yield, and luminous and thermal properties of the product can be adjusted by connecting to differentiated functional groups. The OLED device using the same has a light emitting layer of high fluorescence efficiency and long-term stability, so that luminous efficiency and service life of the OLED device can meet practical demand.

BRIEF DESCRIPTION OF THE DRAWINGS

The above objects and advantages of the present invention will become more readily apparent to those ordinarily skilled in the art after reviewing the following detailed description and accompanying drawings, in which.

DETAILED DESCRIPTION OF PREFERRED EMBODIMENTS

The present invention will now be described more specifically with reference to the following embodiments. It is to be noted that the following descriptions of preferred embodiments of this invention are presented herein for purpose of illustration and description only. It is not intended to be exhaustive or to be limited to the precise form disclosed.

The present invention provides a thermally activated delayed fluorescence material. The thermally activated delayed fluorescence material includes a structure formula 1 as

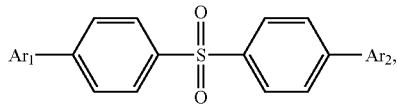

wherein the group Ar1 is identical to or different from the group Ar2, and the group Ar1 and the group Ar2 are consisted of carbazole and/or phenothiazine. In a preferred embodiment, the group Ar1 and the group Ar2 in the structure formula 1 are selected from the following structure formulas:

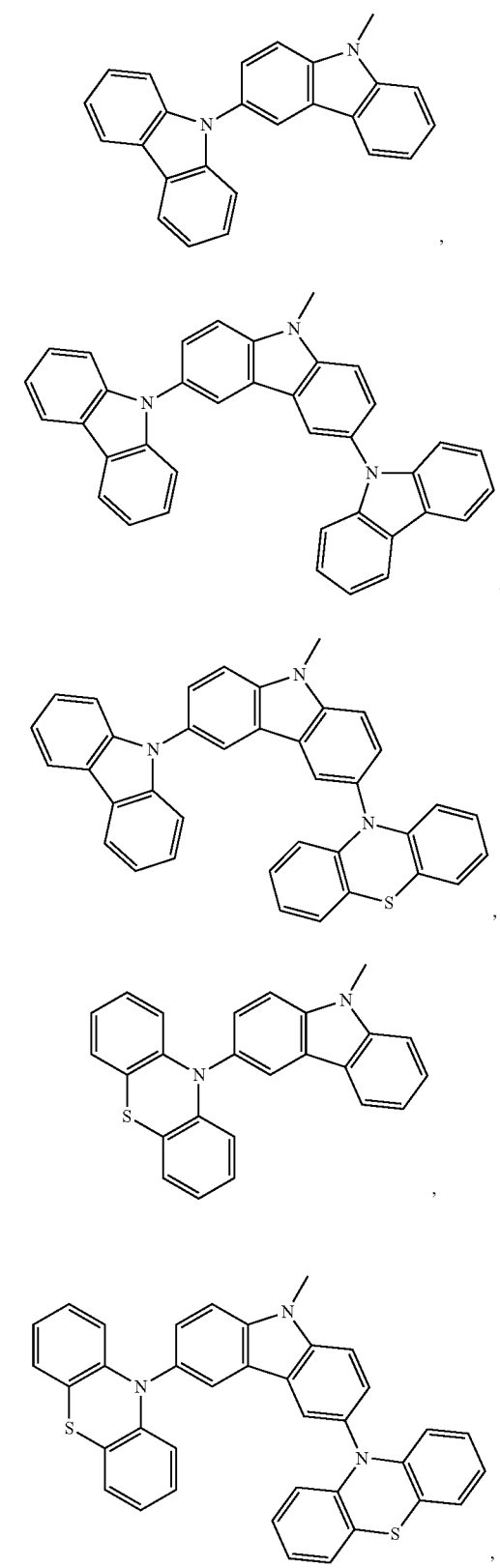

19
-continued
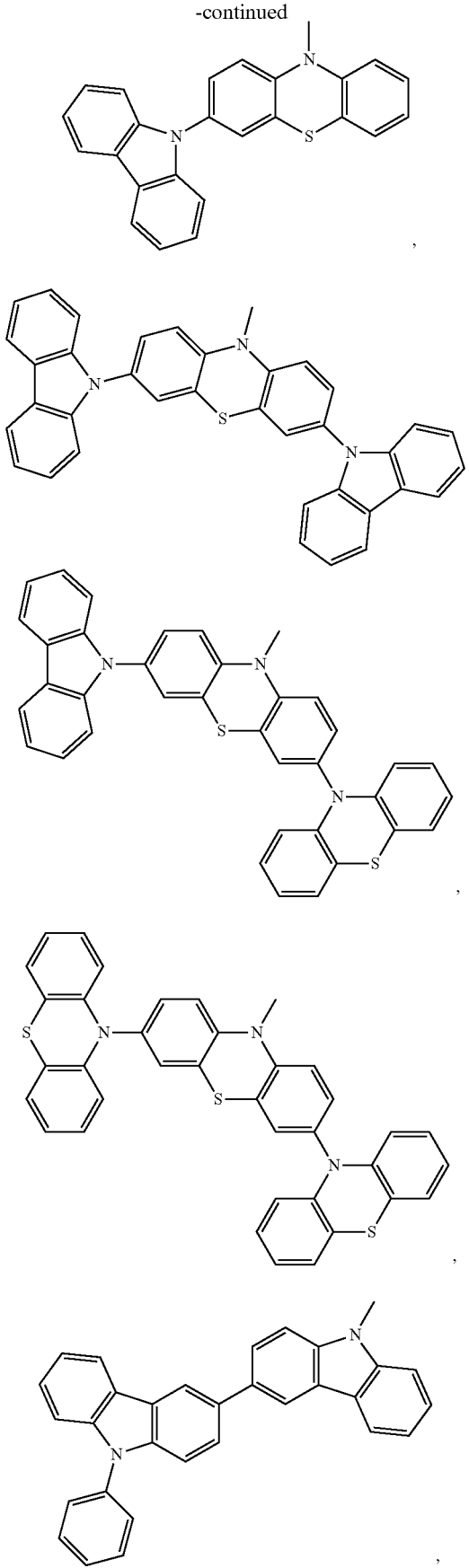
20
-continued
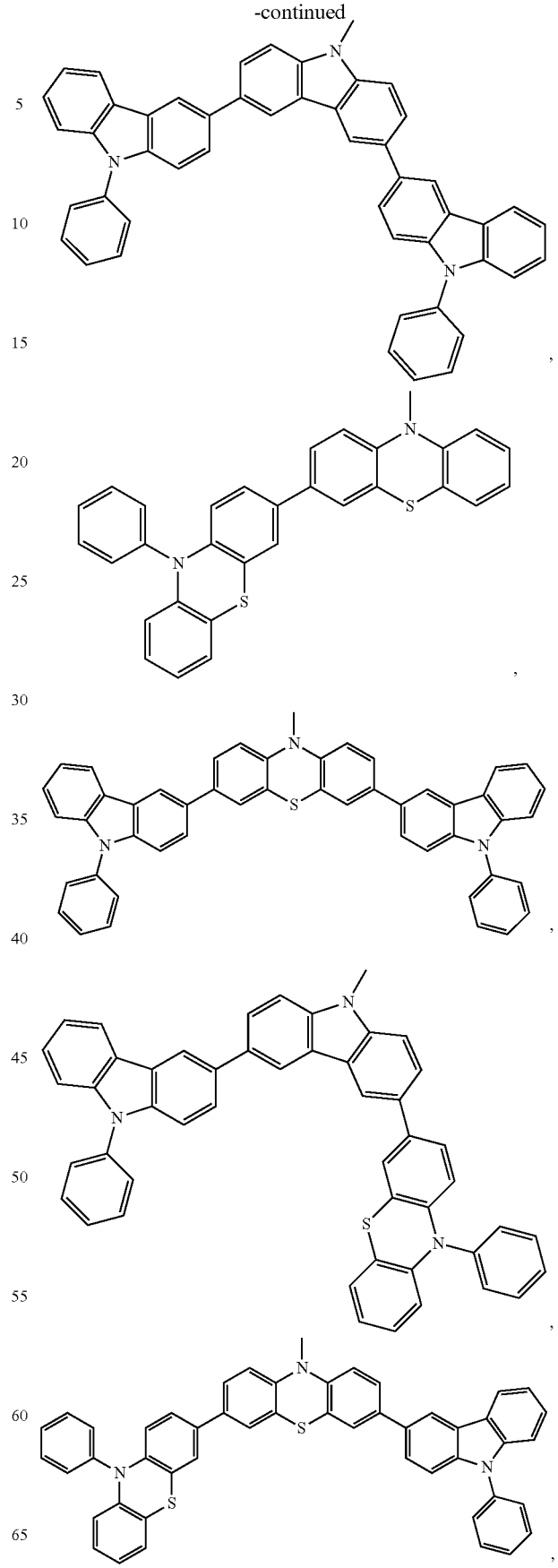

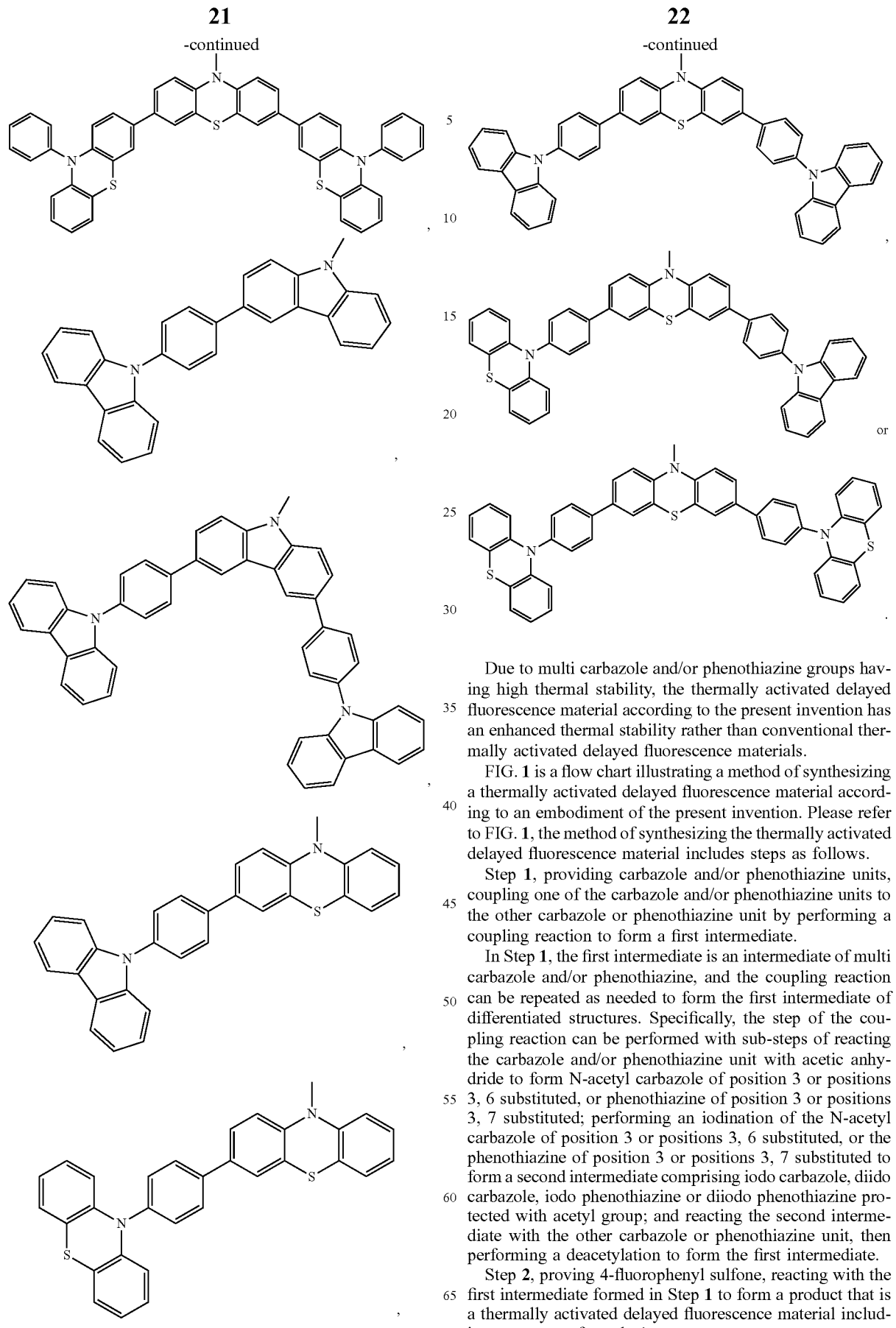

Due to multi carbazole and/or phenothiazine groups having high thermal stability, the thermally activated delayed fluorescence material according to the present invention has an enhanced thermal stability rather than conventional thermally activated delayed fluorescence materials.

Figure 1:
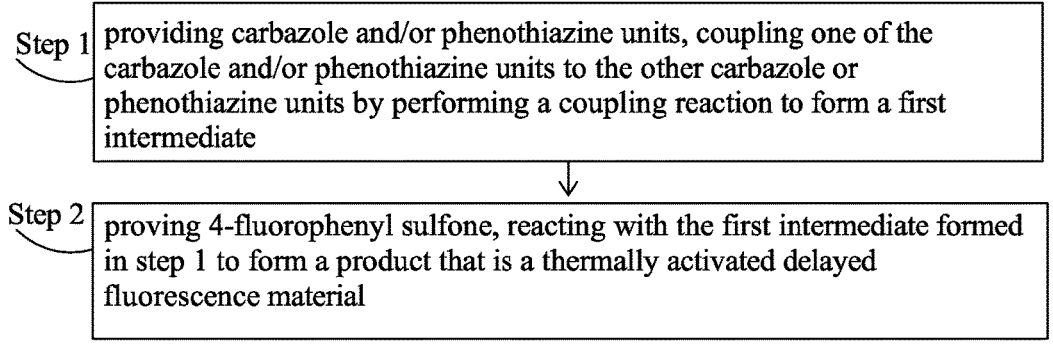
FIG. 1 is a flow chart illustrating a method of synthesizing a thermally activated delayed fluorescence material according to an embodiment of the present invention.

FIG. 1 is a flow chart illustrating a method of synthesizing a thermally activated delayed fluorescence material according to an embodiment of the present invention. Please refer to FIG. 1, the method of synthesizing the thermally activated delayed fluorescence material includes steps as follows.

Step 1, providing carbazole and/or phenothiazine units, coupling one of the carbazole and/or phenothiazine units to the other carbazole or phenothiazine unit by performing a coupling reaction to form a first intermediate.

In Step 1, the first intermediate is an intermediate of multi carbazole and/or phenothiazine, and the coupling reaction can be repeated as needed to form the first intermediate of differentiated structures. Specifically, the step of the coupling reaction can be performed with sub-steps of reacting the carbazole and/or phenothiazine unit with acetic anhydride to form N-acetyl carbazole of position 3 or positions 3, 6 substituted, or phenothiazine of position 3 or positions 3, 7 substituted; performing an iodination of the N-acetyl carbazole of position 3 or positions 3, 6 substituted, or the phenothiazine of position 3 or positions 3, 7 substituted to form a second intermediate comprising iodo carbazole, diido carbazole, iodo phenothiazine or diiodo phenothiazine protected with acetyl group; and reacting the second intermediate with the other carbazole or phenothiazine unit, then performing a deacetylation to form the first intermediate.

Step 2, proving 4-fluorophenyl sulfone, reacting with the first intermediate formed in Step 1 to form a product that is a thermally activated delayed fluorescence material including a structure formula 1 as

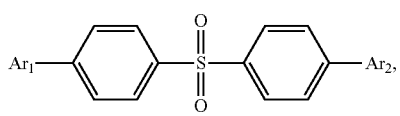

wherein the group Ar1 is identical to or different from the group Ar2, and the group Ar1 and the group Ar2 are consisted of carbazole and/or phenothiazine.

Obviously, the structure of the multi carbazole and/or phenothiazine contained in the first intermediate is corresponding to the group Ar1 and the group Ar2 in the structure formula 1. In Step 2, a product having a symmetrical or asymmetrical molecular structure can be obtained by performing the above said reaction. In case of the group Ar1 identical to the group Ar2, the product has a symmetrical molecular structure; and in case of the group Ar1 different from the group Ar2, the product has an asymmetrical molecular structure.

In an preferred embodiment, the group Ar1 and the group Ar2 in the structure formula 1 are selected from the following structure formulas:

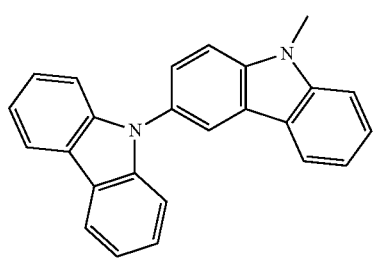

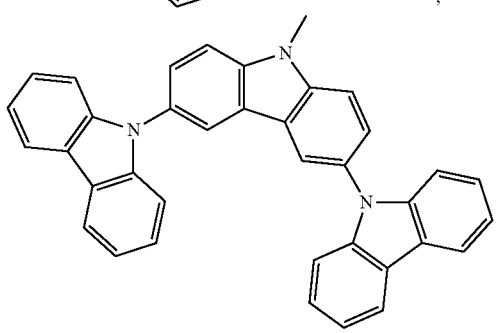

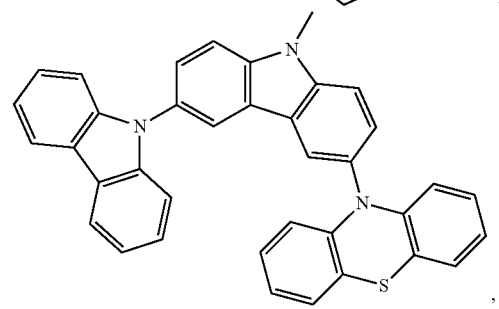

-continued

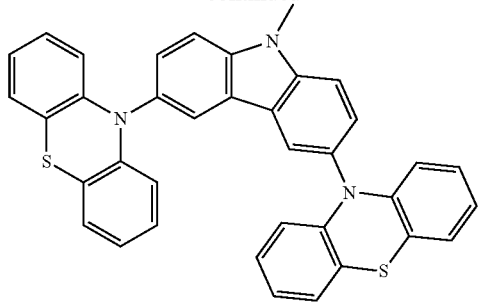

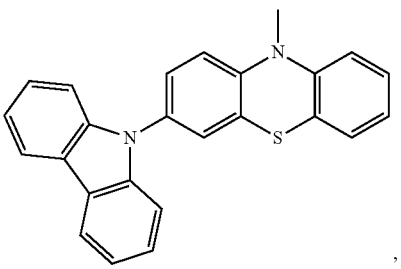

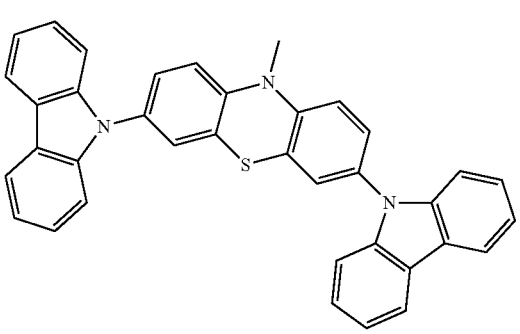

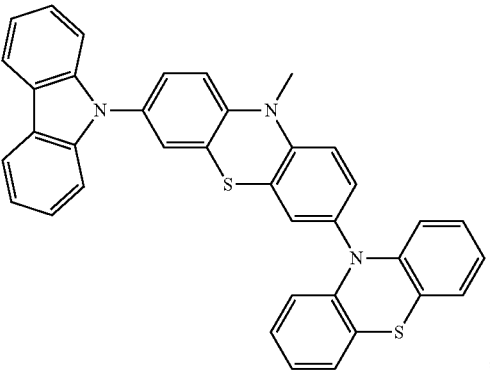

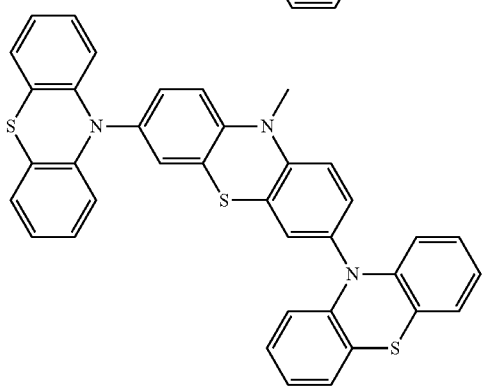

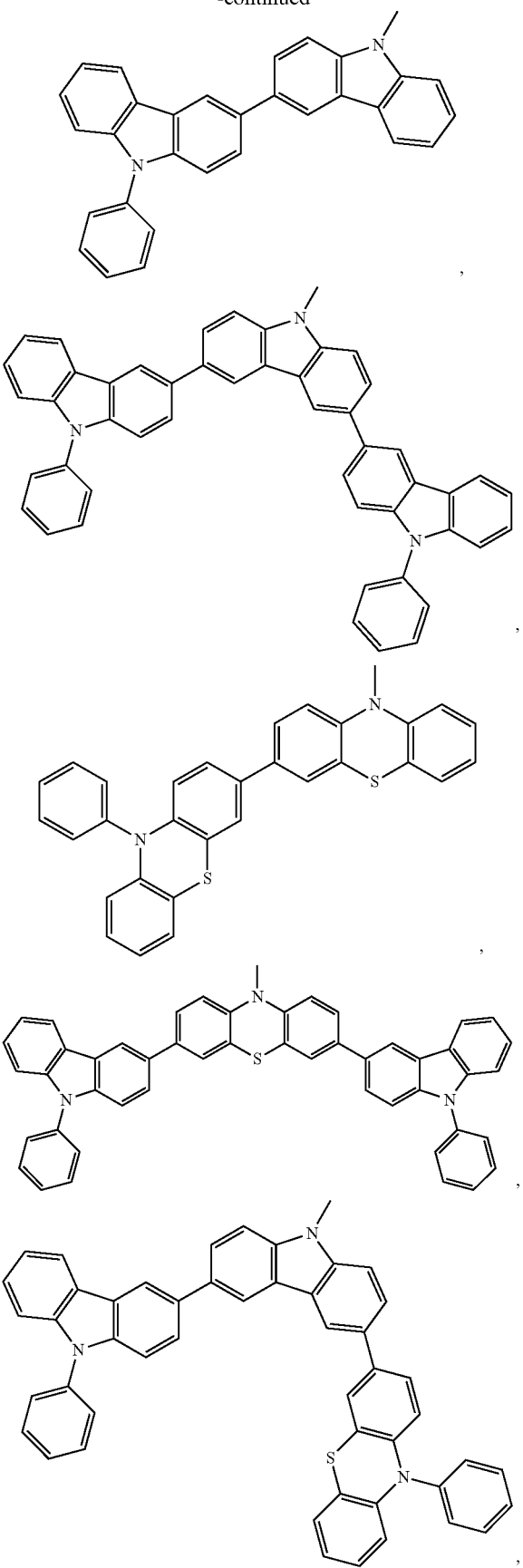
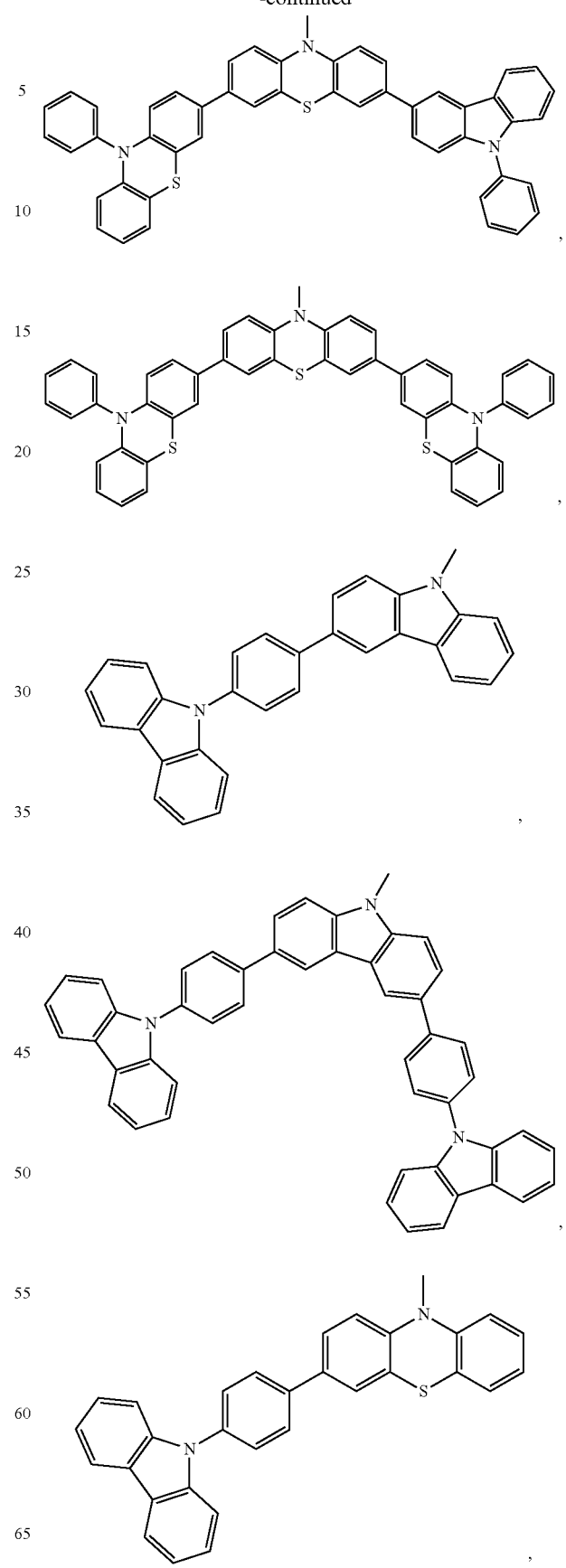

-continued

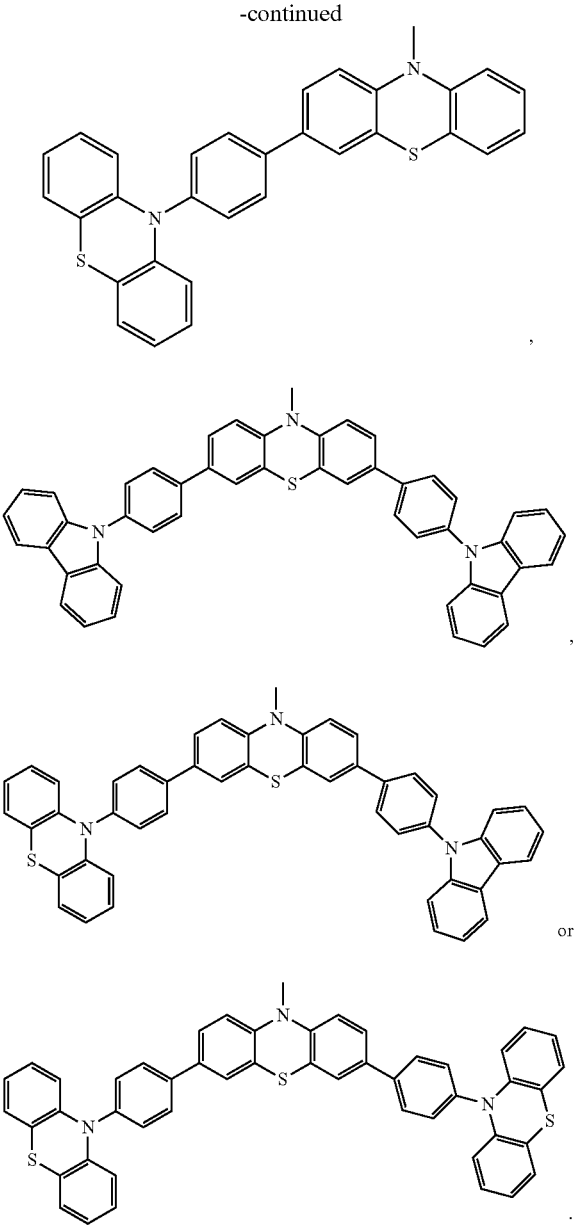
,

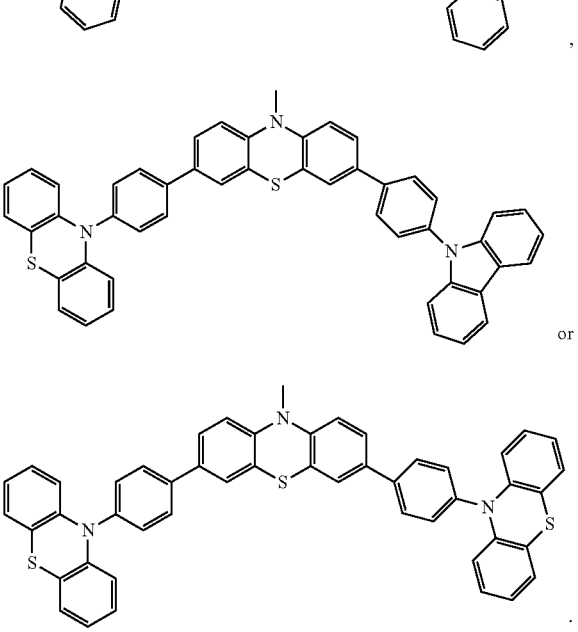
or

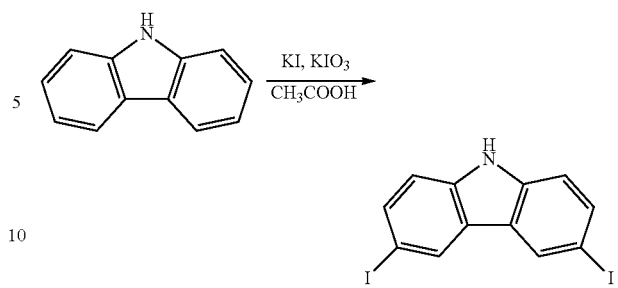

Firstly, 5.0 g carbazole (0.030 mol), 5.0 g potassium periodate (0.023 mol), 6.6 g potassium iodide (0.040 mol) and 50 mL glacial acetic acid are taken and placed into an 100 mL round bottom flask. Then, the 100 mL round bottle flask accommodating the reactants is put in 80° C. water bath, and the reactants is stirred until color of the generated iodine disappeared (about 5 hours). Then, the reactants is cooled down and filtered with Buchner funnel to obtain a crude solid product. The crude solid product is washed with a 200 mL NaHSO₃ solution (5 wt %) to remove the unreacted excess I₂ and KIO₃. After the washed crude product is dried, the dried crude product is recrystallized with ethanol/THF and decolorized with a small amount of activated carbon. Finally, a product that is 9.4 g white crystal (75% yield; melting point, Mp: 210-211° C.) is obtained. It is noted that the reactants of potassium iodate and potassium iodide need to be ground into powder in a mortar before performing the reaction.

2. A route of synthesizing an intermediate of 3,6-diiodo-9-acetyl carbazole is shown as following formula 3.

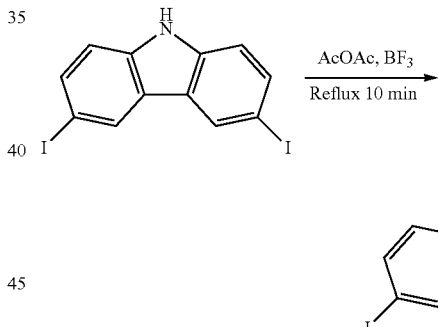

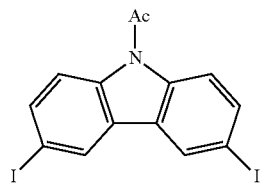

In practical preparation, the structures of the group Ar1 and the group Ar2 can be selected as needed, luminous and thermal properties of the product (i.e. the thermally activated delayed fluorescence material) can be adjusted by connecting to differentiated functional groups.

The method of synthesizing the thermally activated delayed fluorescence material according to the present invention will now be elaborated more specifically with reference to, but not limited to, the following embodiments 1 and 2.

Embodiment 1

A Synthesis of 4,4'-bis(3,6-dicarbazolyl) carbazole diphenyl sulfone

1. A route of synthesizing an intermediate of 3,6-diiodo carbazole is shown as following formula 2.

5.0 g 3,6-diiodo carbazole (0.012 mol) is placed in an 100 mL round bottom flask, 50 mL acetic anhydride and 0.1 mL boron trifluoride diethyl ether are added, the reactants are refluxed for 20 minutes, a heavy white precipitate solid can be seen, and the white precipitate solid is filtered and dried to obtain 5.4 g white product having flour like appearance (98%. yield).

3. A route of synthesizing an intermediate of 3,6-dicarbazol-9-acetyl carbazole is shown as following formula 4.

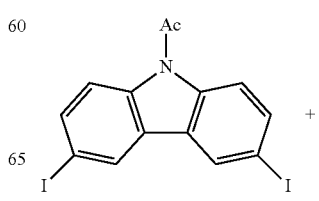

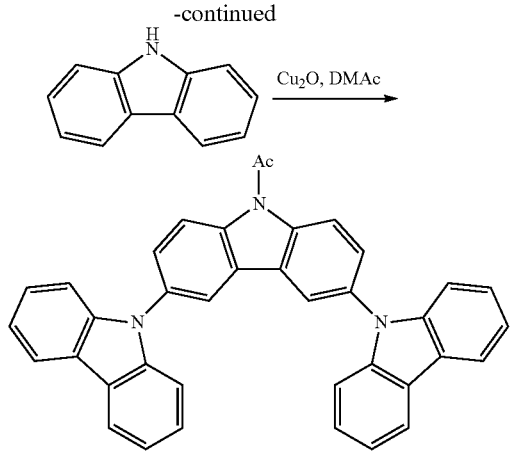
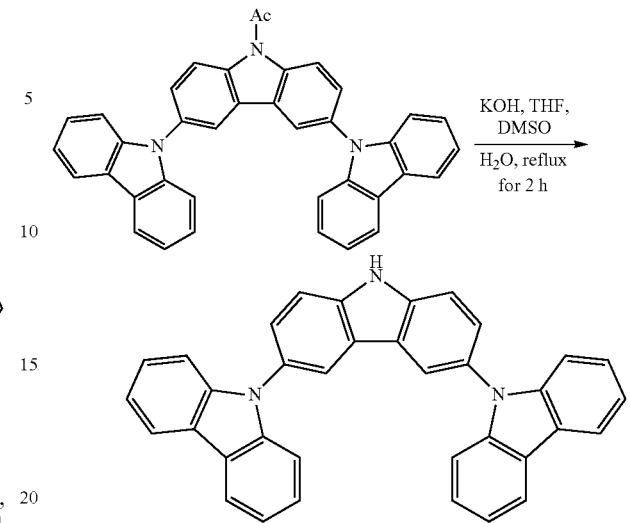

Firstly, 2.4 g 3,6-diiodo-9-acetyl carbazole (5.23 mmol), 2.2 g carbazole (13.2 mmol), 3.0 g cuprous oxide (0.021 mol) and 15 mL DMAc (dimethyl acetamide) are taken and placed in an autoclave, the autoclave accommodating the reactants is vacuumed then poured with nitrogen for three cycles, and reaction of the reactants is performed at 190° C. silicone oil bath for 24 hours. After the reaction is completed, the solution is filtered to obtain a filtrate, the filtrate is then poured into water to precipitate, an appropriate amount of NaCl is added and stirred for half an hour, the filtrate is filtered and dried to obtain a crude product, the crude product is recrystallized with a mixed solvent of EtOH (ethanol) and THF (tetrahydrofuran) (5:1 v/v) and decolorized with a small amount of active carbon, and 1.8 g white crystal is finally obtained (64% yield).

4. A route of synthesizing an intermediate of 3,6-dicarbazolyl carbazole is shown as following formula 5.

Firstly, 2.0 g 3,6-dicarbazol-9-acetyl carbazole (3.7 mmol), 2.0 g KOH (35.7 mmol), 10 mL THF, 5 mL DMSO (dimethyl sulfoxide) and 2 mL water are taken and placed into an 100 mL round bottom flask. Then, the reactants is heated and stirred in reflux reaction for 4 hours, and the reaction process is detected with TLC (Thin Layer Chromatography). After the reaction is completed, the solution is heated to evaporate THF, then poured into water, filtered, precipitated, dried to obtain a crude product, the crude product is recrystallized with EtOH and decolorized with a small amount of activated carbon, and 1.45 g white crystal is finally obtained (95% yield).

5. A route of synthesizing the target compound of 4,4'-bis (3,6-dicarbazolyl) carbazole diphenyl sulfone is shown as following formula 6.

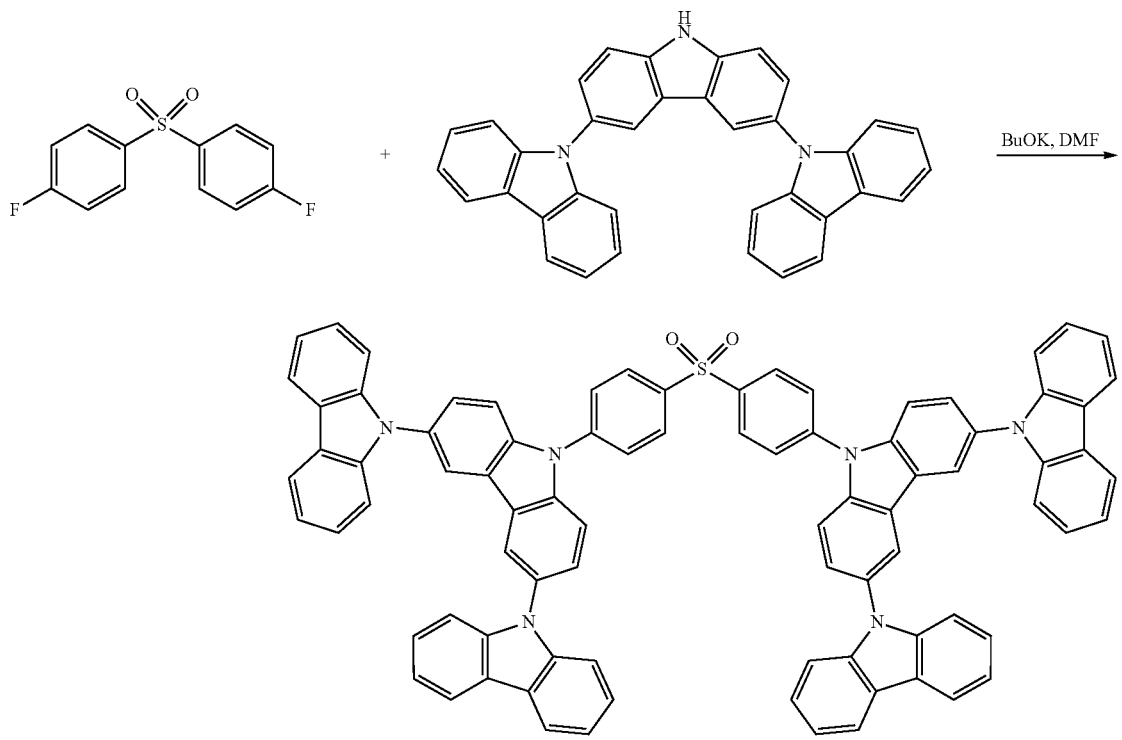

Firstly, the intermediate of 1.4 g 3,6-dicarbazolyl carbazole (0.0028 mol) is taken and dissolved in 20 mL DMF (dimethyl formamide), and 0.32 g potassium t-butoxide (0.003 mol) is added with stirring, the solution is warmed up and kept at 60° C. for 30 minutes, then 0.33 g 4,4'-difluoro diphenyl sulphone (0.0013 mol) is added and reacted, then the reaction of the reactants is performed at 110° C. for 12 hours. After the reaction is completed, the solution is cooled and poured into 200 mL water to precipitate, and the solution is filtrated and repeatedly washed with water to obtain solid. Then, the solid is dissolved in 100 mL dichloromethane to form a solution, an appropriate amount of anhydrous sodium sulfate is added into the solution, and the solution is filtered to obtain a filtrate. Then, 200 mL acetone is added into the filtrate, the filtrate with acetone is distilled to evaporate methylene chloride and most of the acetone by using a rotary evaporator to obtain precipitate, the precipitate is filtered, washed three times with a small amount of acetone and dried under vacuum, and 1.25 g white powder is obtained (80% yield).

Embodiment 2

A Synthesis of 4,4'-bis(3-carbazolyl) carbazole diphenyl sulfone

1. A route of synthesizing an intermediate of 3-iodo carbazole is shown as following formula 7.

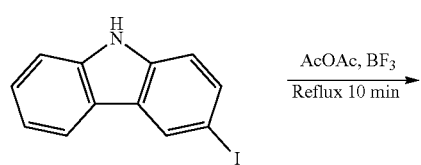

Firstly, 5.0 g carbazole (0.030 mol), 2.5 g potassium periodate (0.0115 mol), 3.3 g potassium iodide (0.020 mol) and 50 mL glacial acetic acid are taken and placed into 100 mL round bottom flask. Then, the 100 mL round bottle flask accommodating the reactants is put in 80° C. water bath, and the reactants is stirred until color of the generated iodine disappeared (about 5 hours). Then, the reactants is cooled down and filtered with Buchner funnel to obtain a crude solid product. The crude solid product is washed with a 200 mL NaHSO3 solution (5 wt %) to remove the unreacted excess $I_2$ and $KIO_3$. After the washed crude product is dried, the dried crude product is recrystallized with ethanol/THF and decolorized with a small amount of activated carbon. Finally, a product that is 6.4 g white crystal (72% yield) is obtained.

2. A route of synthesizing an intermediate of 3-iodo-9-acetyl carbazole is shown as following formula 8.

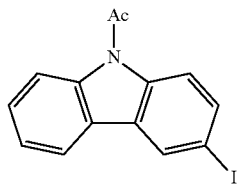

3.5 g 3-iodo carbazole (0.012 mol) is taken and placed in 100 mL round bottom flask, 50 mL acetic anhydride and 0.1 mL boron trifluoride diethyl ether are added, the reactants are refluxed for 20 minutes, a heavy white precipitate solid can be seen, and the white precipitate solid is filtered and dried to obtain 3.8 g white product having flour like appearance (98%. yield).

3. A route of synthesizing an intermediate of 3-carbazol-9-acetyl carbazole is shown as following formula 9.

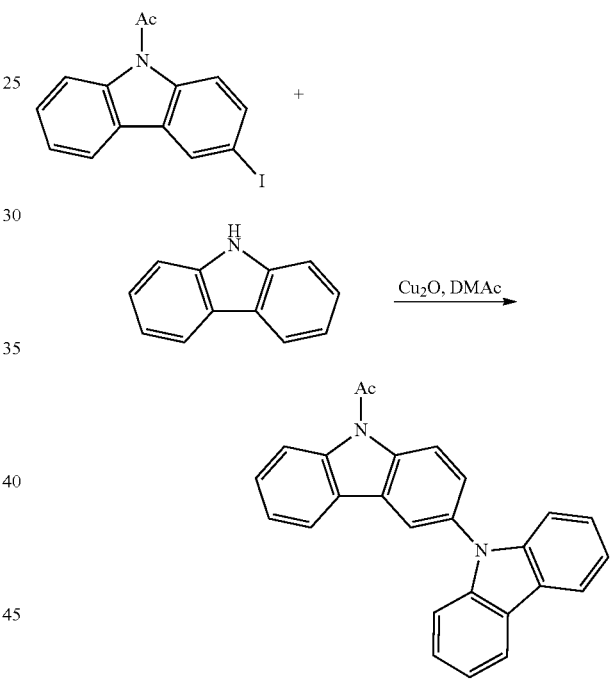

Firstly, 1.75 g 3-iodo-9-acetyl carbazole (5.23 mmol), 0.95 g carbazole (5.23 mmol), 1.5 g cuprous oxide (0.011 mol) and 15 mL DMAc (dimethyl yl-acetamide) are taken and placed in an autoclave, the autoclave accommodating the reactants is vacuumed then poured with nitrogen for three cycles, and reaction of the reactants is performed at 190° C. silicone oil bath for 24 hours. After the reaction is completed, the solution is filtered to obtain a filtrate, the filtrate is then poured into water to precipitate, an appropriate amount of NaCl is added and stirred for half an hour, the filtrate is filtered and dried to obtain a crude product, the crude product is recrystallized with a mixed solvent of EtOH (ethanol) and THF (tetrahydrofuran) (5:1 v/v) and decolorized with a small amount of active carbon, and 1.26 g white crystal is finally obtained (65% yield).

4. A route of synthesizing an intermediate of 3-carbazolyl carbazole is shown as following formula 10.

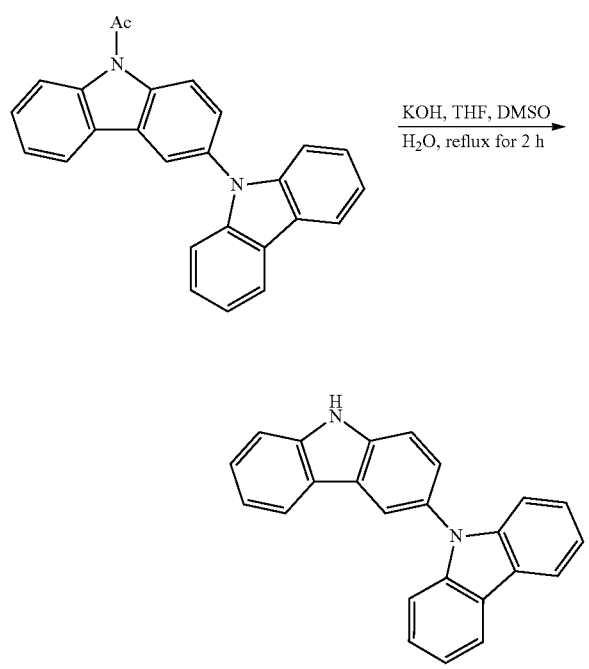

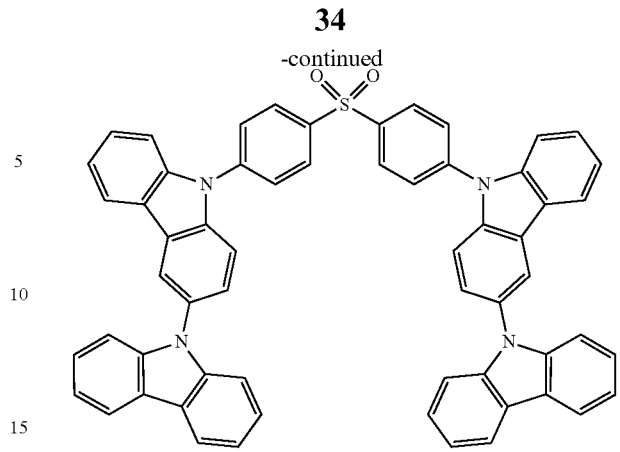

Firstly, the intermediate of 0.92 g 3-carbazolyl carbazole (0.0028 mol) is taken and dissolved in 20 mL DMF (dimethyl formamide), and 0.32 g potassium t-butoxide (0.003 mol) is added with stirring, the solution is warmed up and kept at 60° C. for 30 minutes, then 0.33 g 4,4'-difluoro diphenyl sulphone (0.0013 mol) is added and reacted, then the reaction of the reactants is performed at 110° C. for 12 hours. After the reaction is completed, the solution is cooled and poured into 200 mL water to precipitate, and the solution is filtrated and repeatedly washed with water to obtain solid. Then, the solid is dissolved in 100 mL dichloromethane to form a solution, an appropriate amount of anhydrous sodium sulfate is added into the solution, and the solution is filtered to obtain a filtrate. Then, 200 mL acetone is added into the filtrate, the filtrate with acetone is distilled to evaporate methylene chloride and most of the acetone by using a rotary evaporator to obtain precipitate, the precipitate is filtered, washed three times with a small amount of acetone and dried under vacuum, and 0.90 g white powder is obtained (80% yield).

Figure 2:
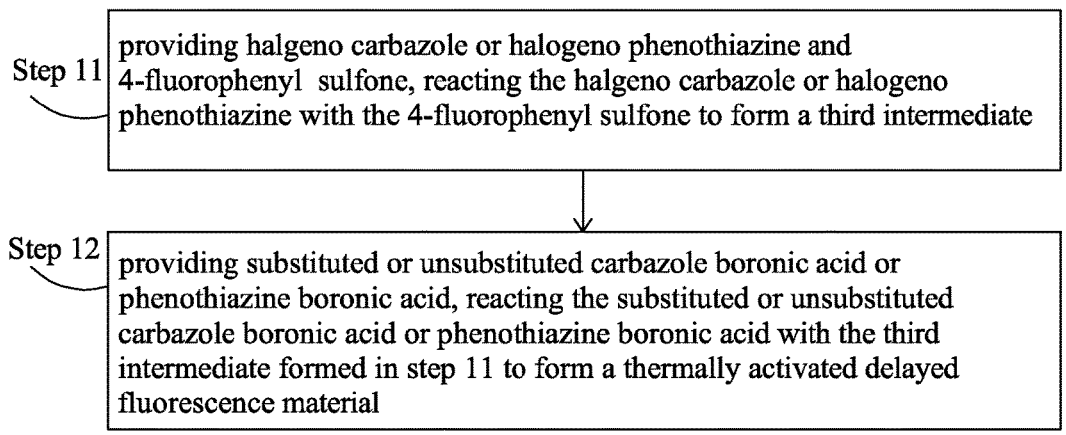
FIG. 2 is a flow chart illustrating a method of synthesizing a thermally activated delayed fluorescence material according to another embodiment of the present invention.

FIG. 2 is a flow chart illustrating a method of synthesizing a thermally activated delayed fluorescence material according to another embodiment of the present invention. Please refer to FIG. 2, the method of synthesizing the thermally activated delayed fluorescence material includes steps as follows.

Step 11, providing halgeno carbazole or halogeno phenothiazine and 4-fluorophenyl sulfone, and reacting the halgeno carbazole or halogeno phenothiazine with the 4-fluorophenyl sulfone to form a third intermediate.

In Step 11, the halgeno carbazole or halogeno phenothiazine is a monohalogenated or dihalogenated compound. In an preferred embodiment, the halgeno carbazole or halogeno phenothiazine is a bromo compound; specifically, the halgeno carbazole is 3-bromo carbazole or 3,6-dibromo carbazole, and the halogeno phenothiazine is 3-bromo phenothizzine or 3,7-dibromo phenothiazine. The halgeno carbazole or halogeno phenothiazine reacts with 4-fluoro phenyl sulfone to form dihalo carbazole diphenyl sulfone or dihalo phenothiazine diphenyl sulfone, i.e. the third intermediate.

Step 12, providing substituted or unsubstituted carbazole boronic acid or phenothiazine boronic acid, reacting the substituted or unsubstituted carbazole boronic acid or phenothiazine boronic acid with the third intermediate to form a thermally activated delayed fluorescence material.

In Step 12, structures of the substituted or unsubstituted carbazole boronic acid or phenothiazine boronic acid can be selected as needed, preferably, such as 9-phenyl-3-carbazole boric acid, boric acid carbazole benzene.

Firstly, 1.38 g 3-carbazol-9-acetyl carbazole (3.7 mmol), 2.0 g KOH (35.7 mmol), 10 mL THF, 5 mL DMSO (dimethyl sulfoxide) and 2 mL water are taken and placed into an 100 mL round bottom flask. Then, the reactants is heated and stirred in reflux reaction for 4 hours, and the reaction process is detected with TLC (Thin Layer Chromatography). After the reaction is completed, the solution is heated to evaporate THF, then poured into water, filtered, precipitated, dried to obtain a crude product, the crude product is recrystallized with EtOH and decolorized with a small amount of activated carbon, and 0.97 g white crystal is finally obtained (95% yield).

5. A route of synthesizing the target compound of 4,4'-bis (3-carbazolyl) carbazole diphenyl sulfone is shown as following formula 11.

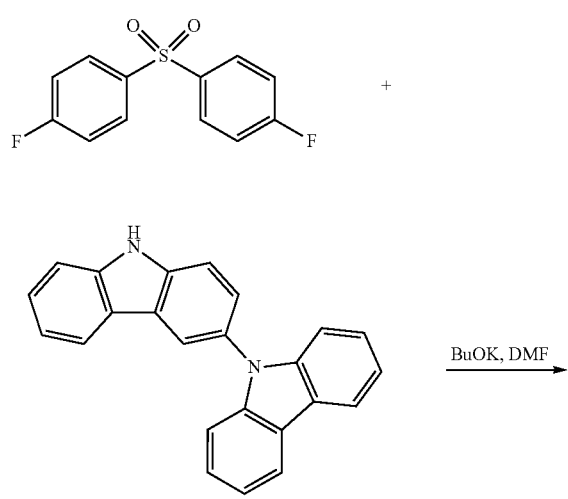

The method of synthesizing the thermally activated delayed fluorescence material according to the present invention will now be elaborated more specifically with reference to, but not limited to, the following embodiments 3 and 4.

Embodiment 3

A Synthesis of 4,4'-bis(3-phenyl carbazole) carbazole diphenyl sulfone

1. A route of synthesizing an intermediate of dibromo carbazole diphenyl sulfone is shown as following formula 12.

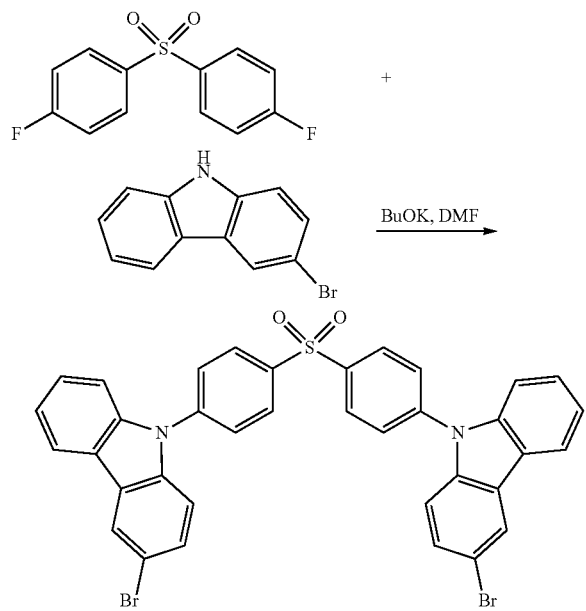

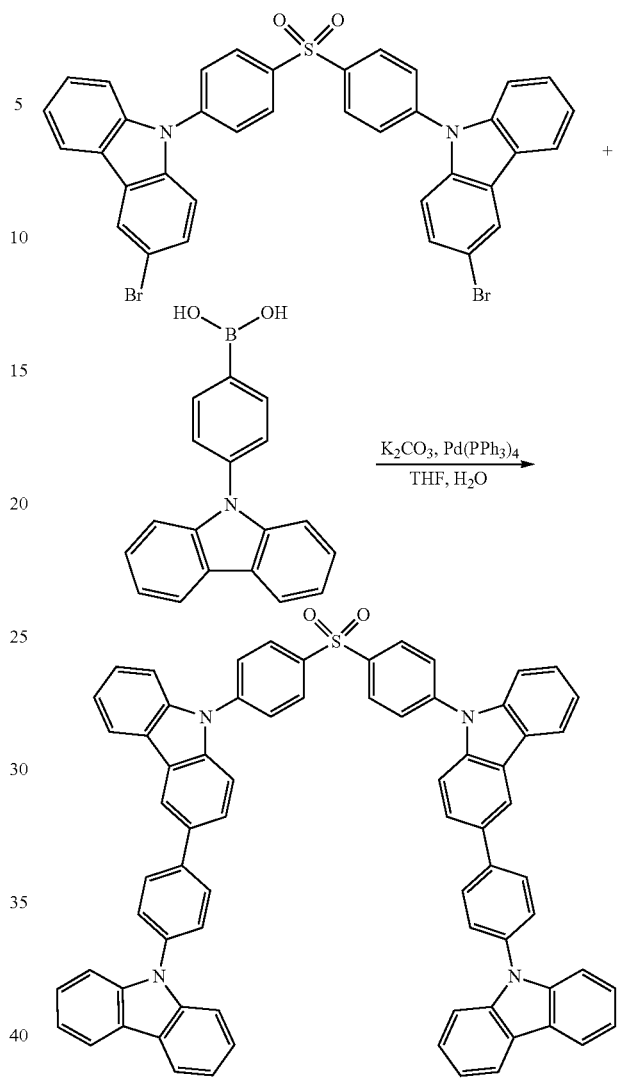

Firstly, the intermediate of 6.5 g 3-bromocarbazole (0.028 mol) is taken and dissolved in 100 mL DMF (dimethyl formamide), and 3.2 g potassium t-butoxide (0.03 mol) is added with stirring, the solution is warmed up and kept at 60° C. for 30 minutes, then 3.3 g 4,4'-difluoro-diphenyl sulphone (0.013 mol) is added and reacted, then the reaction of the reactants is performed at 110° C. for 12 hours. After the reaction is completed, the solution is cooled and poured into 600 mL water to precipitate, and the solution is filtrated and repeatedly washed with water to obtain solid. Then, the solid is dissolved in 100 mL dichloromethane to form a solution, an appropriate amount of anhydrous sodium sulfate is added into the solution, and the solution is filtered to obtain a filtrate. Then, 200 mL acetone is added into the filtrate, the filtrate with acetone is distilled to evaporate methylene chloride and most of the acetone by using a rotary evaporator to obtain precipitate, the precipitate is filtered, washed three times with a small amount of acetone and dried under vacuum, and 7.3 g white powder is obtained (80% yield).

2. A route of synthesizing an intermediate of 4,4'-bis(3-phenyl carbazole) carbazole diphenyl sulfone is shown as following formula 13.

Firstly, 1.196 g the intermediate of dibromo carbazole diphenyl sulfone (0.0017 mol), 1.09 g carbazole phenyl boronic acid (0.0038 mol) are taken and placed into a three-necked flask, 40 mL THF and 8 mL $K_2CO_3$ solution (2M) are added into the three-necked flask, stirred and poured with argon for 30 minutes, 0.01 g $Pd(PPh_3)_4$ is added, the three-necked flask accommodating the reactants is put in an oil bath, and the reactants are heated to react at 90° C. for 24 hours. After the reaction is completed, the solution is extracted with water, organic phase of the extracted solution is dried with anhydrous sodium sulfate, and a crude product is obtained through a vacuum rotary drying process with a rotary evaporator. Then, the crude product is purified by using silica gel column chromatography with a mixed solution of n-hexane and dichloromethane (1:1 volume ratio) as an eluent. Then, a pure product of 1.31 g white powder is obtained (75% yield).

Embodiment 4

A Synthesis of 4,4'-bis(3-phenyl carbazolyl) carbazole diphenyl sulfone

A route of synthesizing 4,4'-bis(3-phenyl carbazolyl) carbazole diphenyl sulfone is shown as following formula 14.

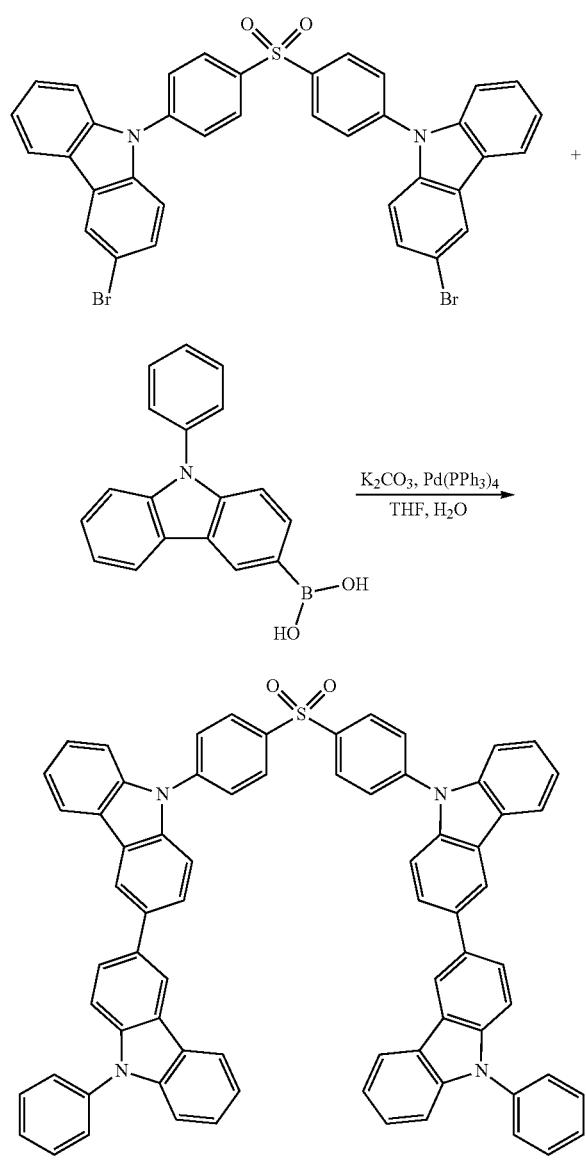

oil bath, and the reactants are heated to react at 90° C. for 24 hours. After the reaction is completed, the solution is extracted with water, organic phase of the extracted solution is dried with anhydrous sodium sulfate, and a crude product is obtained through a vacuum rotary drying process with a rotary evaporator. Then, the crude product is purified by using silica gel column chromatography with a mixed solution of n-hexane and dichloromethane (1:1 volume ratio) as an eluent. Then, a pure product of 1.35 g white powder is obtained (77% yield).

Embodiment 5 a synthesis of an intermediate of 3,6-phenothiazinyl-9-acetyl carbazole (61% yield) is similar to the method described in Embodiment 1 except the carbazole in the step 3 that is replaced by phenothiazine. A route of synthesizing 3,6-diphenothiazinyl-9-acetyl carbazole is shown as following formula 15.

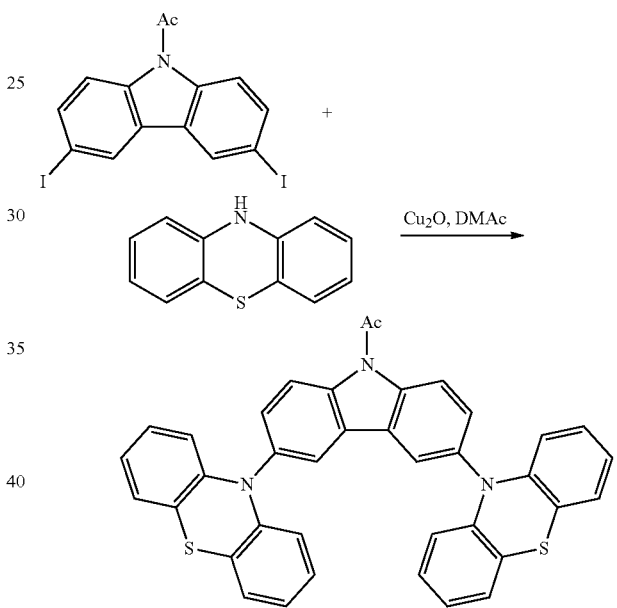

Firstly, 1.196 g the intermediate of dibromo carbazole diphenyl sulfone (0.0017 mol), 1.09 g 9-phenyl-3 carbazole boric acid (0.0038 mol) are taken and placed into a three-necked flask, 40 mL THF and 8 mL K$_2$CO$_3$ solution (2M) are added into the three-necked flask, stirred and poured with argon for 30 minutes, 0.01 g Pd(PPh$_3$)$_4$ is added, the three-necked flask accommodating the reactants is put in an Then, according to the steps 4 and 5 described in Embodiment 1, a target compound of 4,4'-bis(3,6-diphenothiazinyl) carbazole diphenyl sulfone is obtained, wherein a yield of the step 4 is 93%, a yield of the step 5 is 79%, and a route of synthesizing the target compound of 4,4'-bis(3,6-diphenothiazinyl) carbazole diphenyl sulfone is shown as following formula 16.

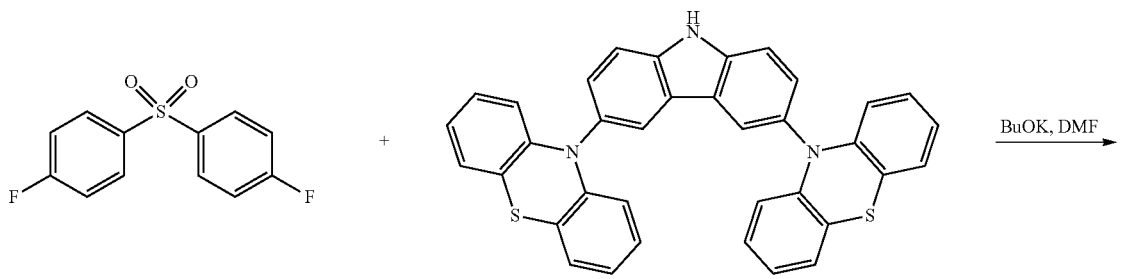

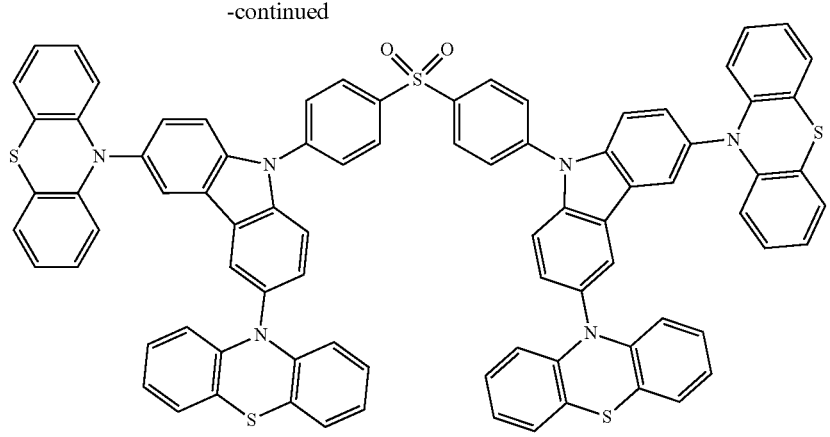

Embodiment 6 a synthesis of 4,4'-bis(3-diphenothiazinyl) carbazole diphenyl sulfone is similar to the method described in Embodiment 2 except the carbazole in the step 3 that is replaced by phenothiazine. Then, according to the steps 4 and 5 described in Embodiment 2, a target compound of 4,4'-bis(3-phenothiazinyl) carbazole diphenyl sulfone is obtained. A route of synthesizing the target compound of 4,4'-bis(3-phenothiazinyl) carbazole diphenyl sulfone is shown as following formula 17.

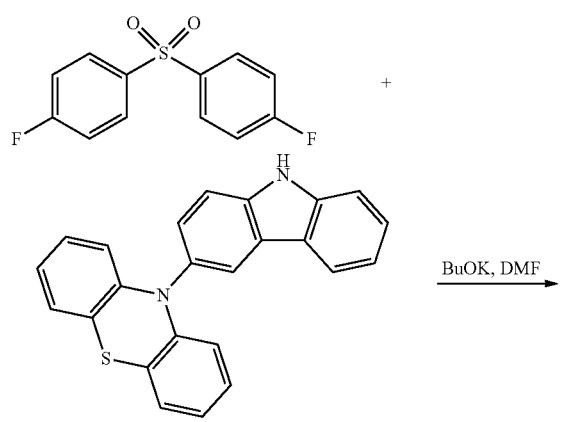

Embodiment 7 a synthesis of 4,4'-bis(3,7-dicarbazolyl) phenothiazine diphenyl sulfone

According to the method described in Embodiment 1 except the carbazole in the step 1 that is replaced by phenothiazine, an intermediate of 3,7-diiodo phenothiazine is obtained; then, the reactions as described in Embodiment 1 are sequentially performed so that a target compound of 4,4'-bis(3,7-dicarbazolyl) phenothiazine diphenyl sulfone is obtained. A route of synthesizing the target compound of 4,4'-bis(3,7-dicarbazolyl) phenothiazine diphenyl sulfone is shown as following formula 18.

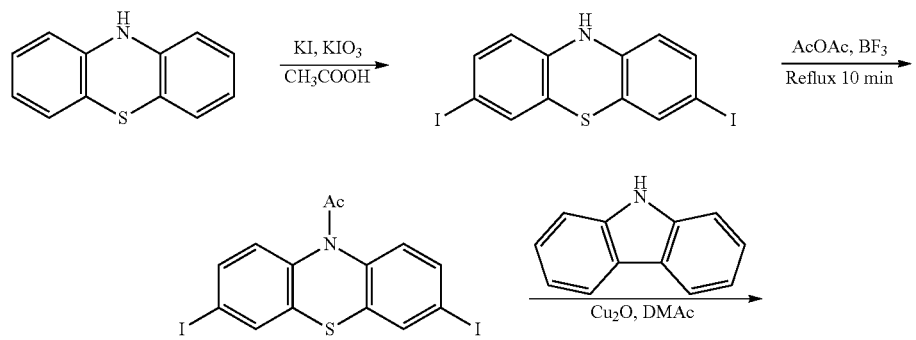

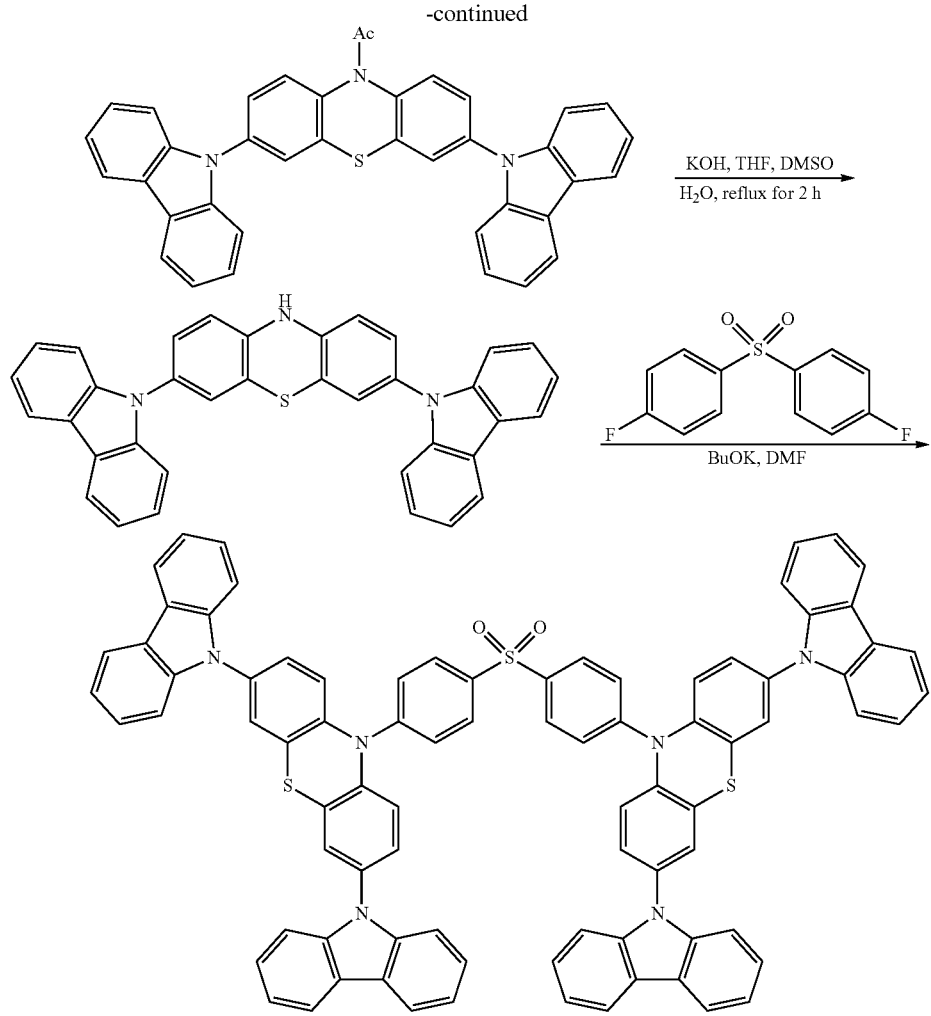

Control Embodiment 1

Firstly, 3.34 g carbazole (0.02 mol), 2.55 g 4,4'-difluoro diphenyl sulfone (0.01 mol) are taken and placed into a three-necked flask, 100 mL N, N-dimethyl formamide (DMF) and 2.24 g potassium tert-butoxide (0.02 mol) are added into the three-necked flask, stirred and poured with argon, and the reactants are heated to react at 90° C. for 24 hours. After the reaction is completed, the solution is extracted with water and dichloromethane, organic phase of the extracted solution is dried with anhydrous sodium sulfate, and a crude product is obtained through a vacuum rotary drying process with a rotary evaporator. Then, the crude product is purified by using silica gel column chromatography with a mixed solution of n-hexane and dichloromethane (a certain volume ratio) as an eluent. Then, a product is obtained (85% yield). A route of Control Embodiment 1 is shown as following formula 19.

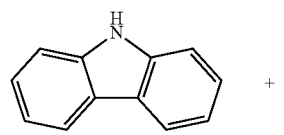
+

Control Embodiment 2

With reference to the synthesizing method of Control Embodiment 1, a yield of Control Embodiment 2 is 82%, and a route of Control Embodiment 2 is shown as following formula 20.

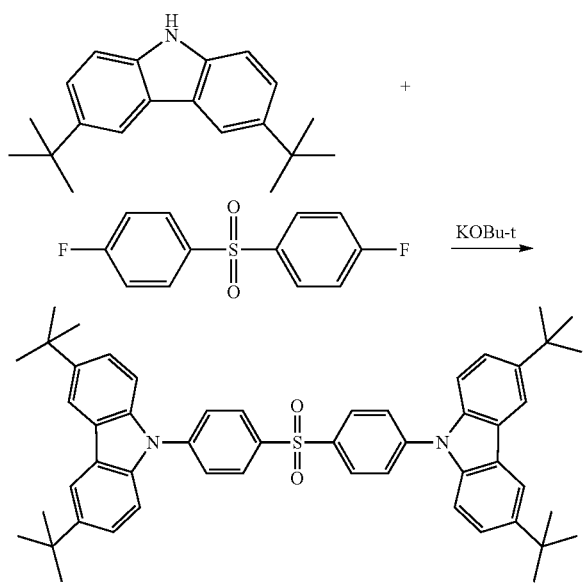

For further describing performance of the thermally activated delayed fluorescence material according to the present invention, a property test of the products (i.e. target compounds) of Embodiments 1-4 is performed. The main items in the property test are thermal property and maximum fluorescence emission wavelength, and the test results are shown in Table 1.

TABLE 1

| compound | Tg (° C.) | Td (° C.) | $\lambda_{max}^{em}$ (nm) | $\Phi_F$ |
|---|---|---|---|---|
| Embodiment 1 | 230 | 422 | 438 | 25% |
| Embodiment 2 | 211 | 405 | 429 | 30% |
| Embodiment 3 | 201 | 320 | 454 | 32% |
| Embodiment 4 | 207 | 350 | 411 | 40% |
| Embodiment 5 | 234 | 420 | 470 | 29% |
| Embodiment 6 | 215 | 410 | 445 | 31% |
| Embodiment 7 | 237 | 438 | 465 | 27% |
| Control Embodiment 1 | 125 | 321 | 419 | 32% |
| Control Embodiment 2 | 130 | 333 | 408 | 25% |

In the property test, the test of weight loss temperature Td is measured at 1% weight loss in 20 mL/min nitrogen by using a thermal analyzer (TGA-50H, Shimadzu Corp., Japan); the test of glass transition temperature Tg is measured with a differential scanning calorimetry (DSC) by using a differential scanning calorimeter (DSC204F1, NETZSCH company, German) at 10° C./min heating rate; the test of maximum fluorescence emission wavelength $\lambda_{max}^{em}$ of powder sample uses a fluorescence spectrophotometer (RF-5301pc, Shimadzu Corp., Japan); the test of fluorescence quantum efficiency $\Phi_F$ of powder sample uses a fiber optic spectrometer (a solid fluorescence quantum efficiency test system consisted of Maya 2000Pro, U.S. Ocean Optics, American Blue Philippine's C-701 integrating sphere and U.S. Ocean Optics LLS-LED light source, according to a test method disclosed in the literature Adv. Mater. 1997, Method 9, 230-232).

Based on the results in Table 1, the thermally activated delayed fluorescence material according to the present invention has a better thermal stability, higher glass transition temperature and stronger luminous intensity. Therefore, the thermally activated delayed fluorescence material according to the present invention is very suitable for use of forming a light emitting layer material in OLED devices.

Figure 3:
FIG. 3 is a schematic cross-section view illustrating an OLED device using a thermally activated delayed fluorescence material according to the present invention.

For the above aspect, the present invention provides an OLED device using the thermally activated delayed fluorescence. FIG. 3 is a schematic cross-section view illustrating an OLED device using a thermally activated delayed fluorescence material according to the present invention. Please refer to FIG. 3, the OLED device using the same includes a substrate 10, a transparent conductive layer 20, a hole transport layer 30, a light emitting layer 40, an electron transport layer 50 and a metal layer 60. The transparent conductive layer 20 is formed on the substrate 10. The hole transport layer 30 is formed on the transparent conductive layer 20. The light emitting layer 40 is formed on the hole transport layer 30. The electron transport layer 50 is formed on the light emitting layer 40. The metal layer 60 is formed on the electron transport layer 50. The light emitting layer 40 includes a thermally activated delayed fluorescence material as a light emitting material of the light emitting layer 40.

In conclusion, the thermally activated delayed fluorescence material according to the present invention combines multi carbazole and/or phenothiazine of high thermal stability so as to have a higher glass transition temperature, high thermal stability and excellent luminous efficiency. The method of synthesizing the same has simplified steps, easily purified product, high yield, and luminous and thermal properties of the product can be adjusted by connecting to differentiated functional groups. The OLED device using the same has a light emitting layer of high fluorescence efficiency and long-term stability, so that luminous efficiency and service life of the OLED device can meet practical demand.

While the invention has been described in terms of what is presently considered to be the most practical and preferred embodiments, it is to be understood that the invention needs not be limited to the disclosed embodiment. On the contrary, it is intended to cover various modifications and similar arrangements included within the spirit and scope of the appended claims which are to be accorded with the broadest interpretation so as to encompass all such modifications and similar structures.

What is claimed is:

1. A thermally activated delayed fluorescence material, comprising a structure formula 1 as

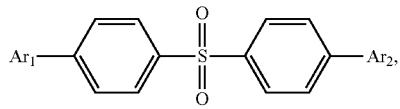

wherein the group Ar$_1$ is identical to or different from the group Ar$_2$, and the group Ar$_1$ and the group Ar$_2$ are selected from the following structure formulas:

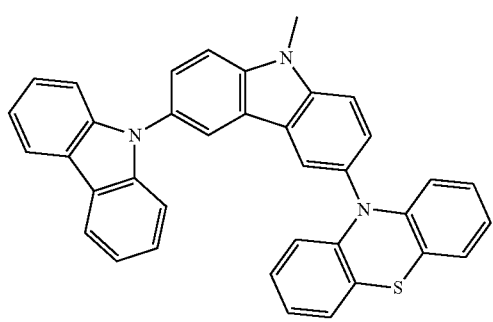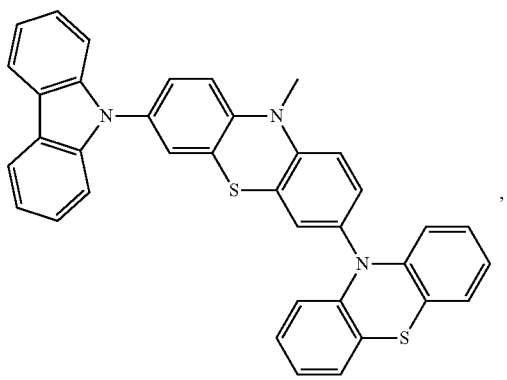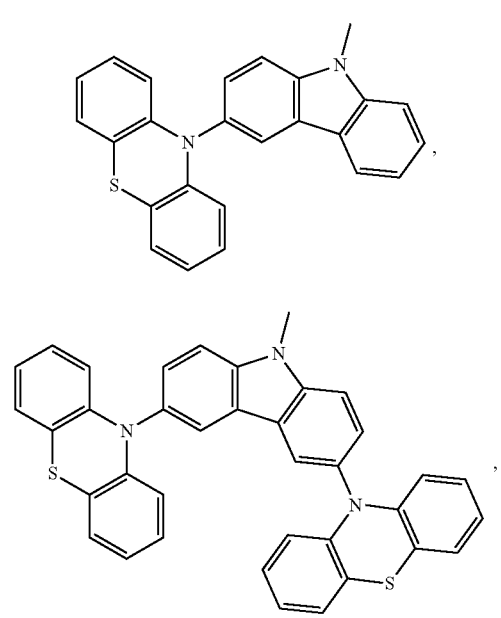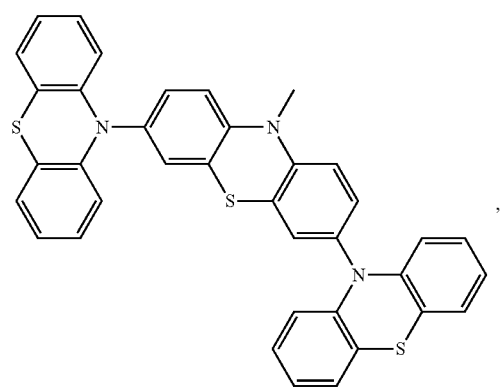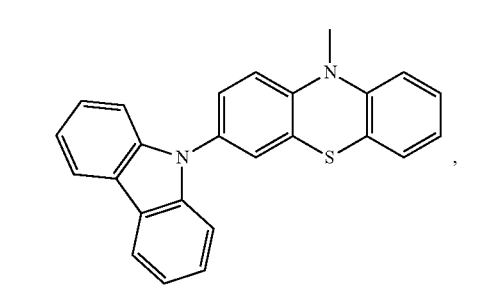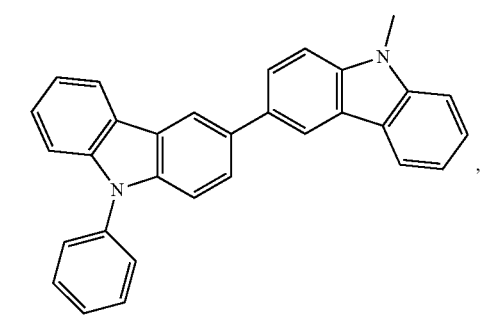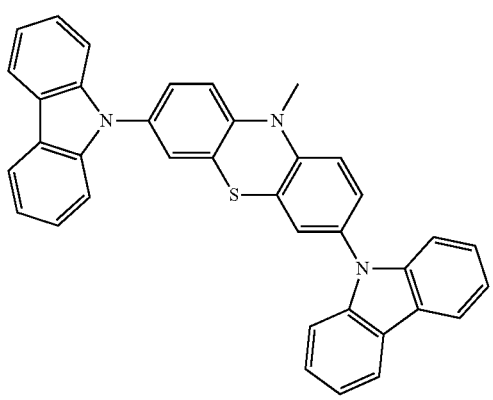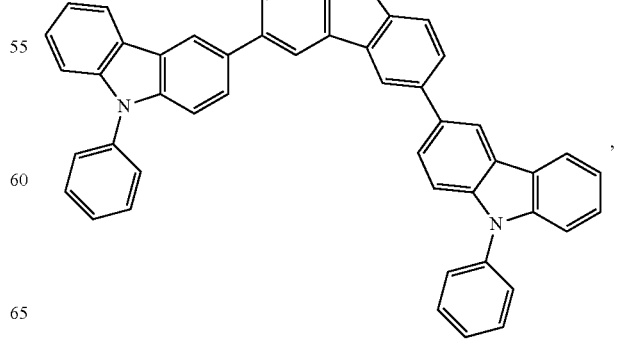

47
-continued
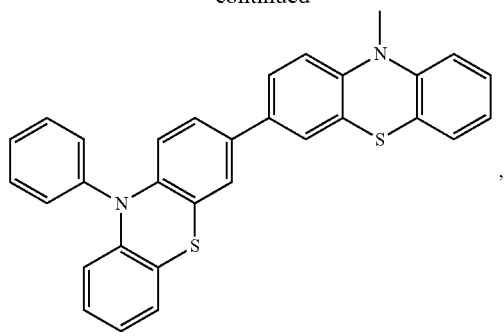
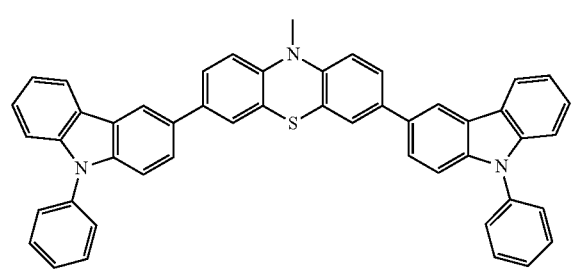
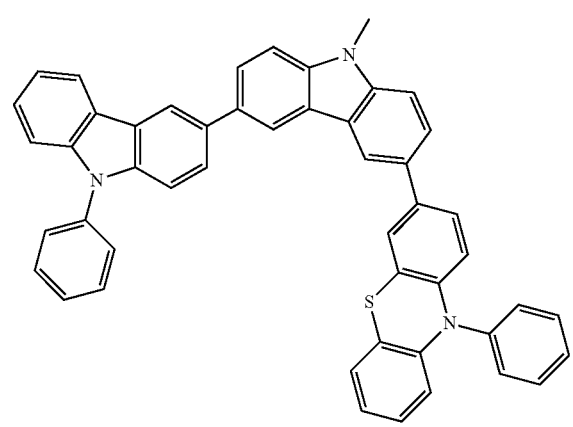
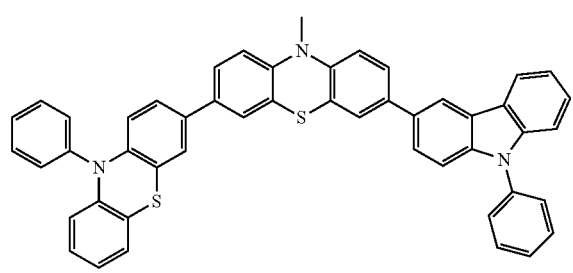
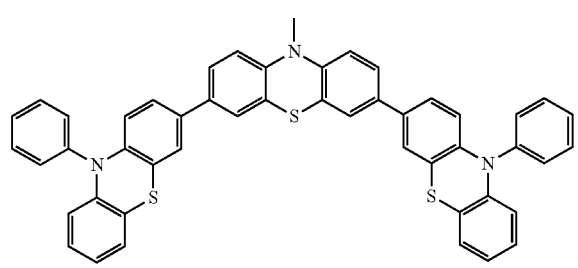
48
-continued
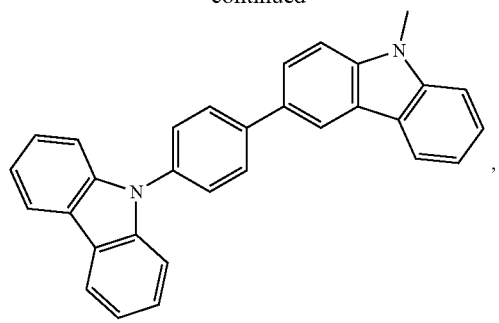
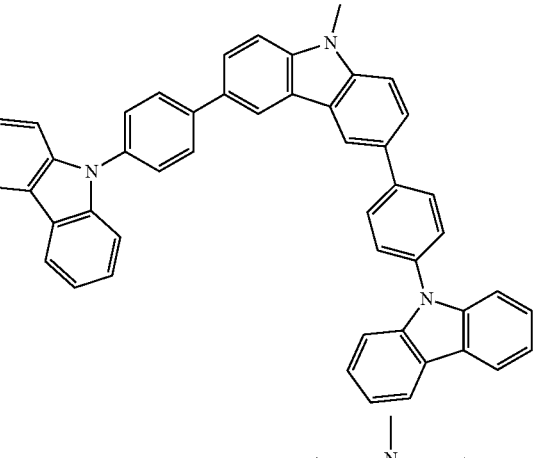
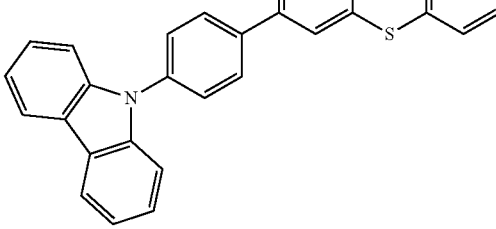
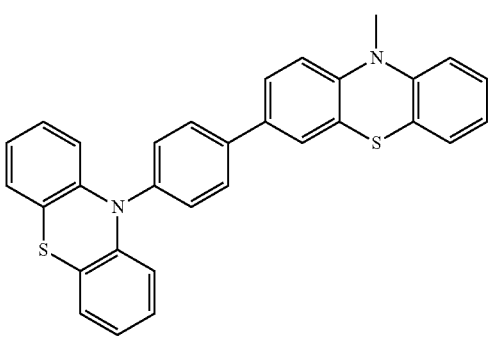
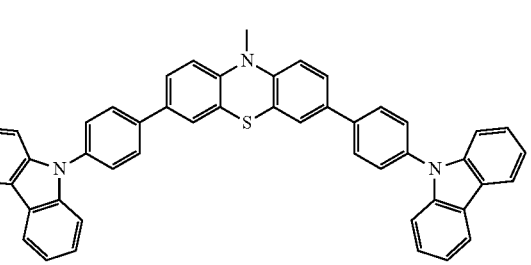

-continued

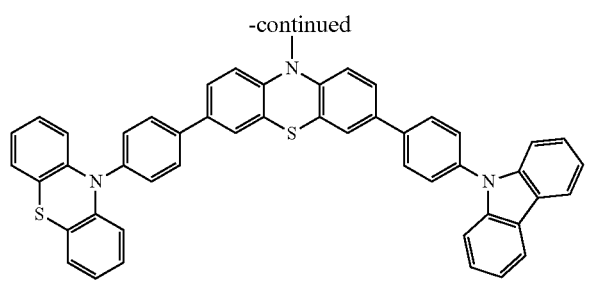

or

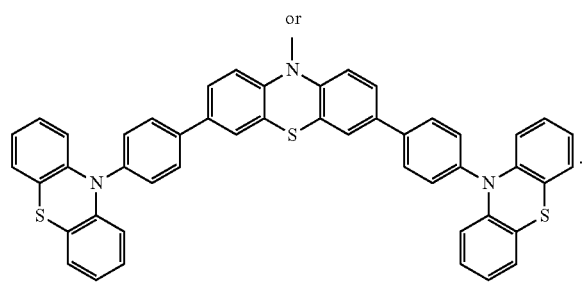

2. A method of synthesizing a thermally activated delayed fluorescence material, comprising steps as follows:

Step 1, providing at least two carbazole and/or phenothiazine units, coupling one of the carbazole and/or phenothiazine units to the other carbazole or phenothiazine unit by performing a coupling reaction to form a first intermediate; and Step 2, proving 4-fluorophenyl sulfone, reacting the 4-fluorophenyl sulfone with the first intermediate formed in Step 1 to form a product that is a thermally activated delayed

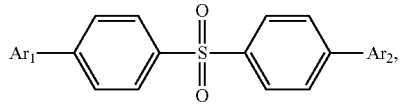

fluorescence material comprising a structure formula 1 as wherein the group $Ar_1$ is identical to or different from the group $Ar_2$, and the group $Ar_1$ and the group $Ar_2$ are selected from the following structure formulas:

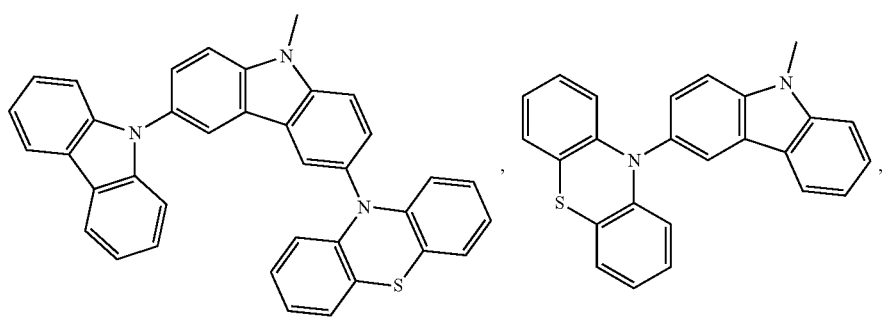

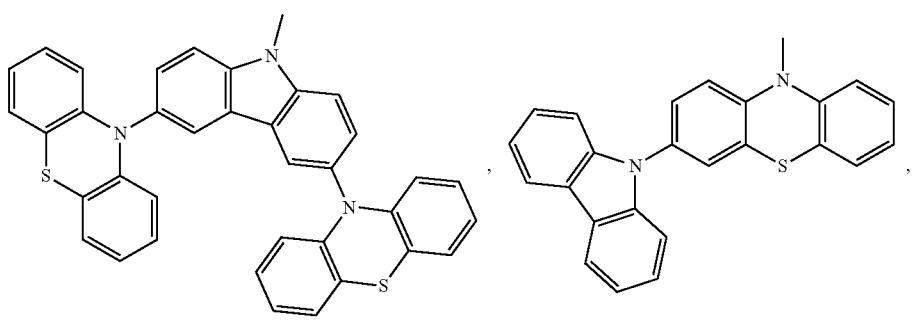

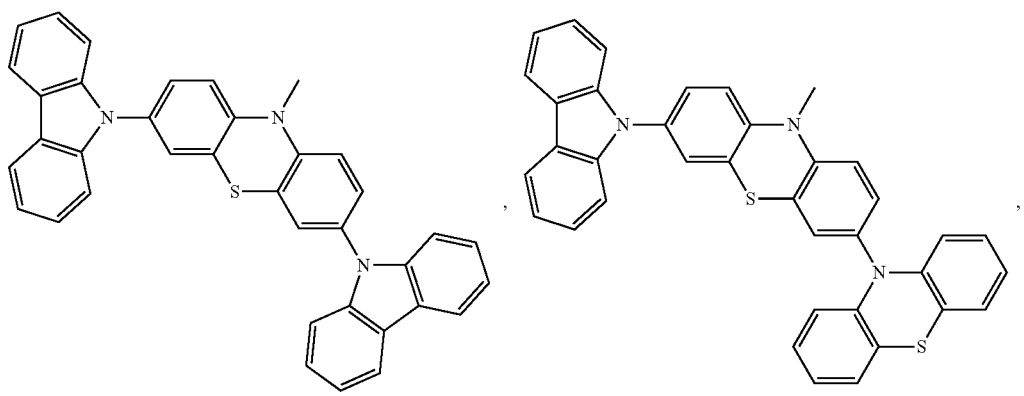

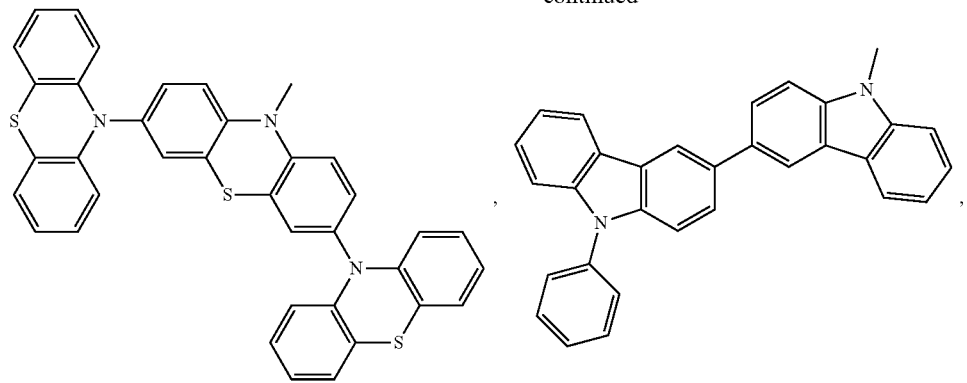
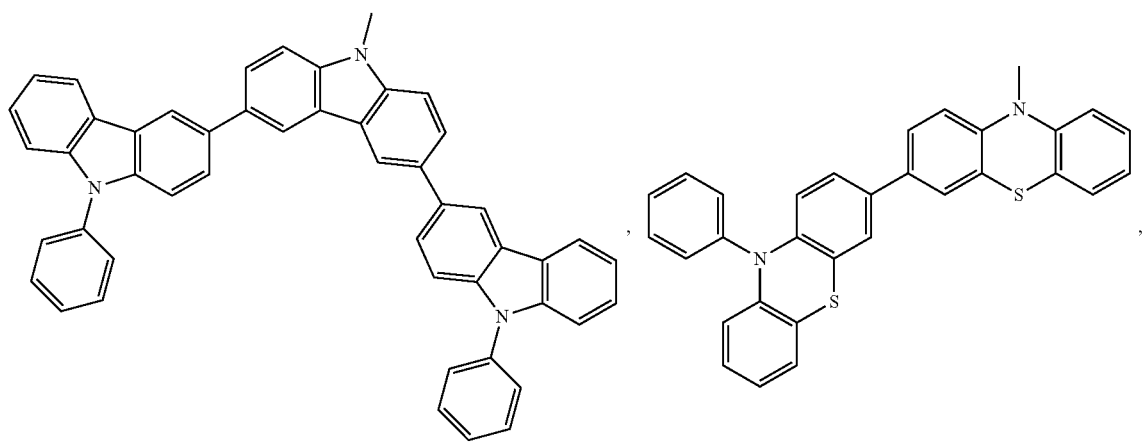
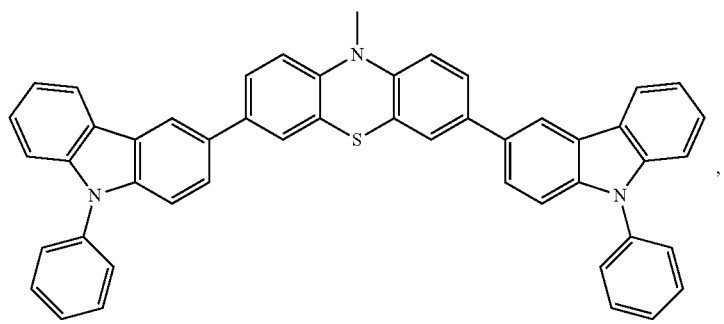
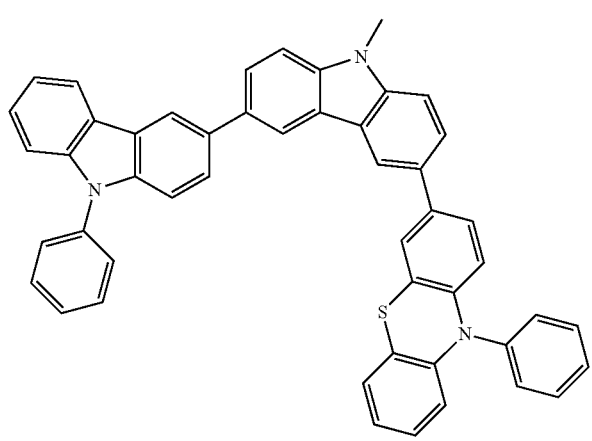

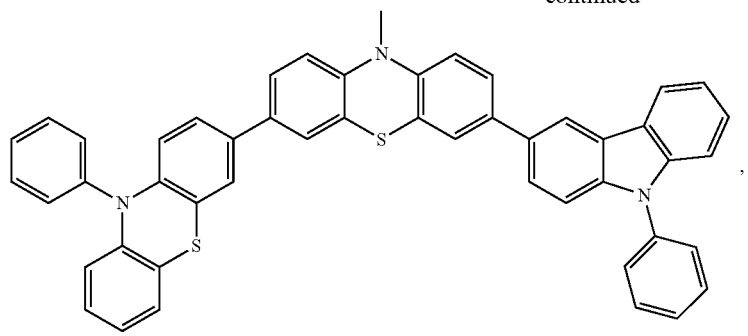
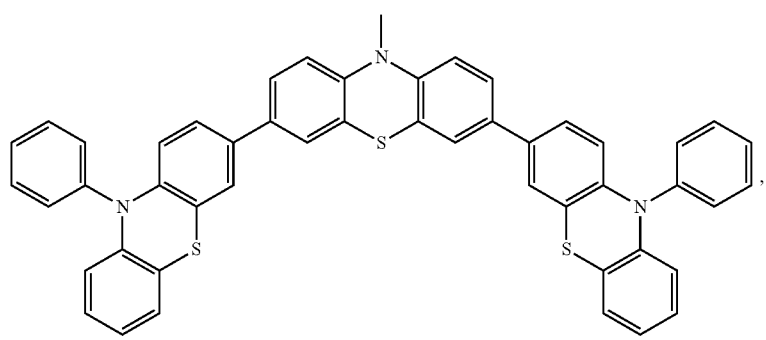
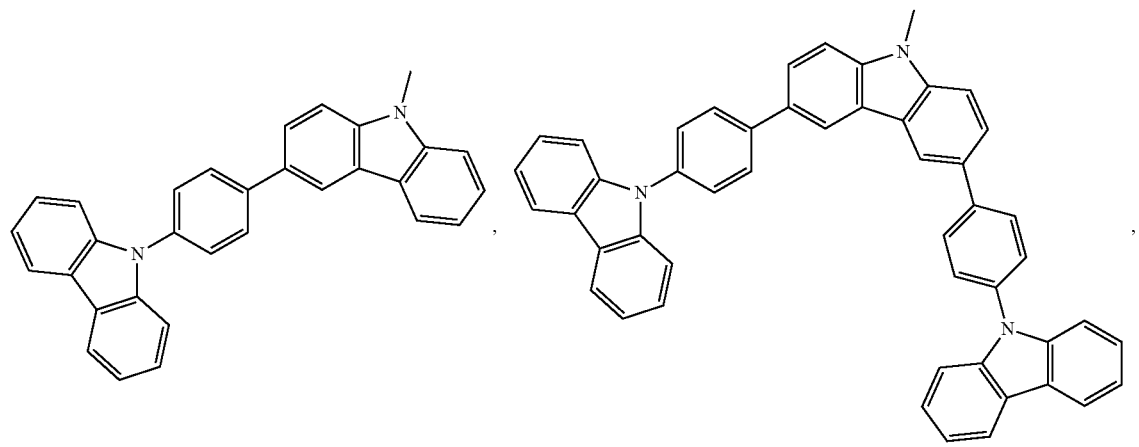
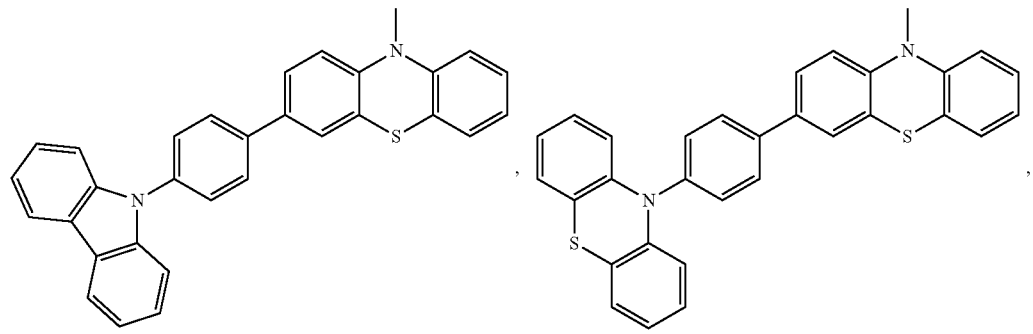

-continued

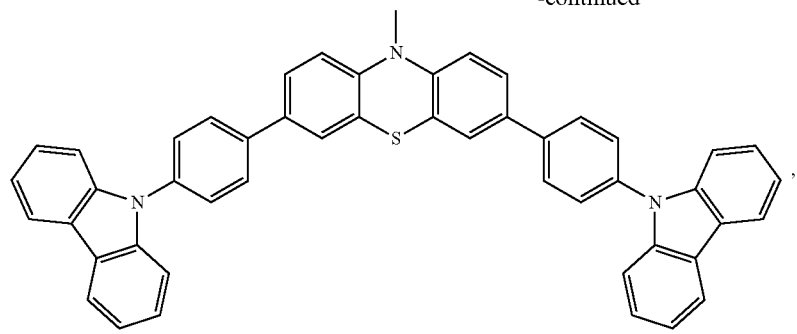

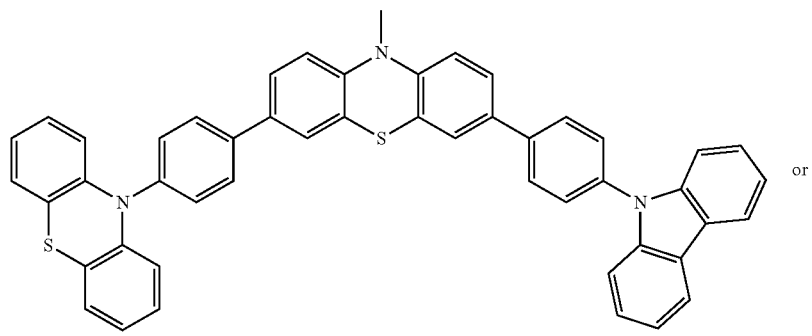

or

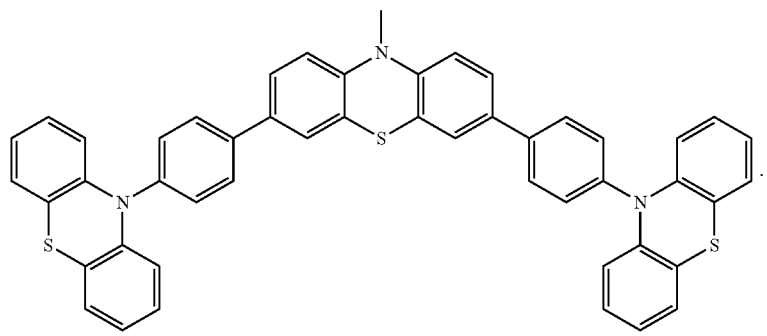

3. A method of synthesizing a thermally activated delayed fluorescence material, comprising steps as follows:
  Step 1, providing halgeno carbazole or halogeno phenothiazine and 4-fluorophenyl sulfone, reacting the halgeno carbazole or halogeno phenothiazine with the 4-fluorophenyl sulfone to form a third intermediate; and
  Step 1, providing substituted or unsubstituted carbazole boronic acid or phenothiazine boronic acid, reacting the substituted or unsubstituted carbazole boronic acid or phenothiazine boronic acid with the third intermediate formed in Step 11 to form a thermally activated delayed fluorescence material comprising a structure formula 1 as

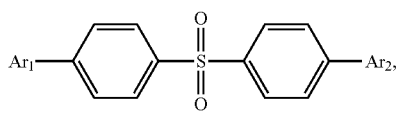

wherein the group Ar$_1$ is identical to or different from the group Ar$_2$, and the group Ar$_1$ and the group Ar$_2$ are consisted of carbazole and/or phenothiazine.

4. The method according to claim 3, wherein the halgeno carbazole or halogeno phenothiazine is a monohalogenated or dihalogenated compound, and the halgeno carbazole or halogeno phenothiazine is a bromo compound.

5. The method according to claim 4, wherein the halgeno-carbazole is 3-bromo carbazole or 3,6-dibromo carbazole, and the halogeno phenothiazine is 3-bromo phenothizzine or 3,7-dibromo phenothiazine.

6. The method according to claim 3, wherein the group Ar$_1$ and the group Ar$_2$ are selected from the following structure formulas:

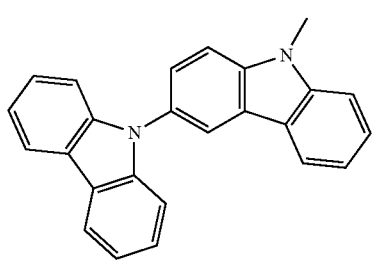

57
-continued
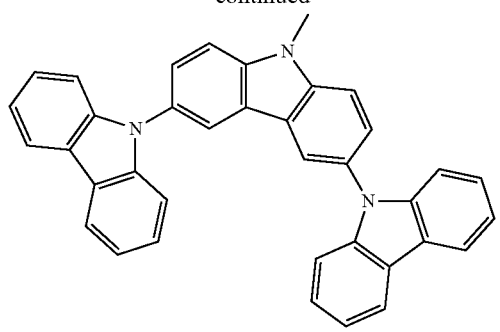
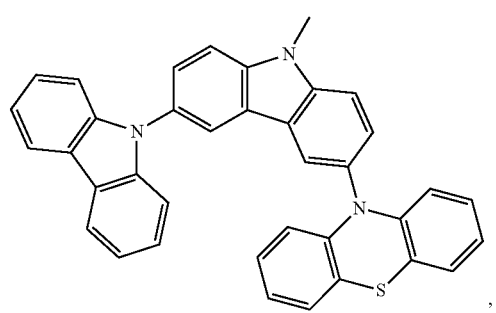
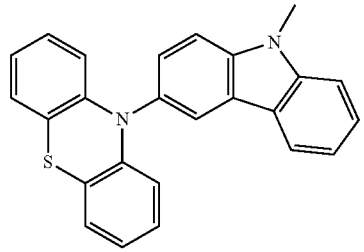
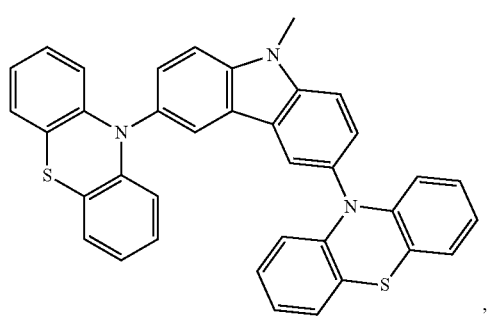
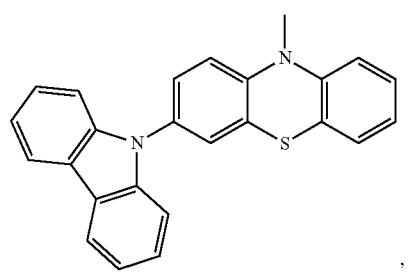
58
-continued
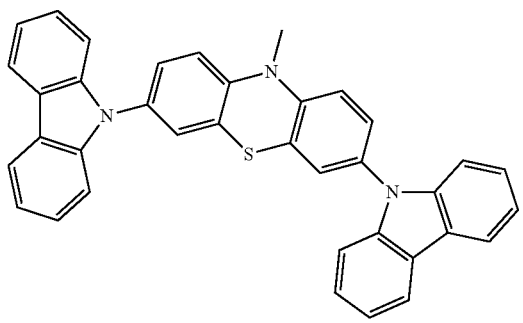
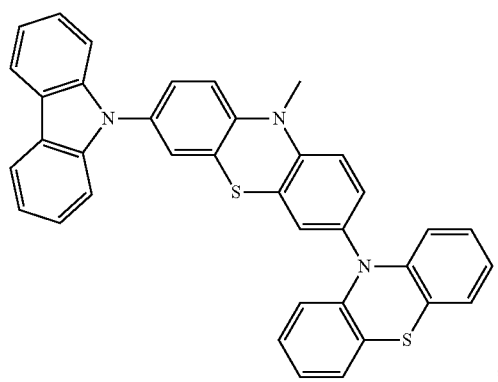
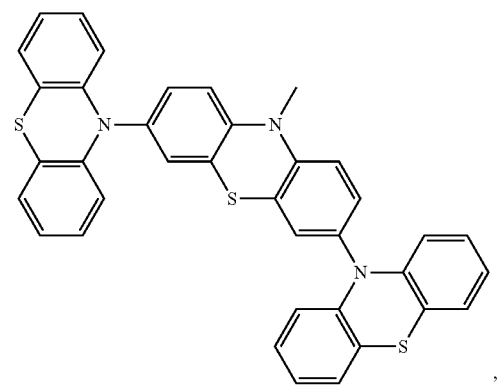
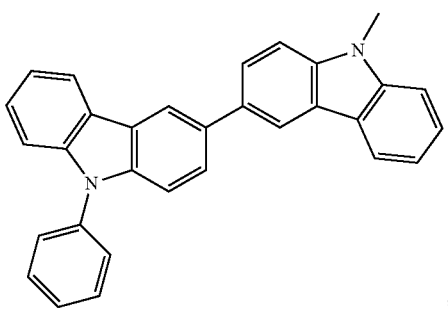

-continued

-continued

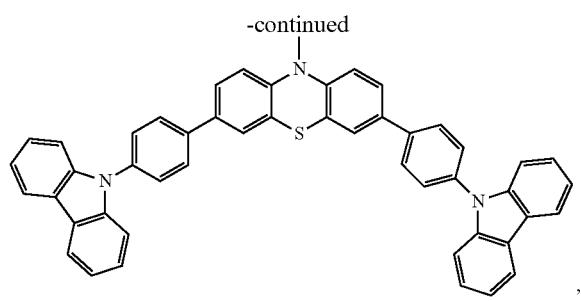

,

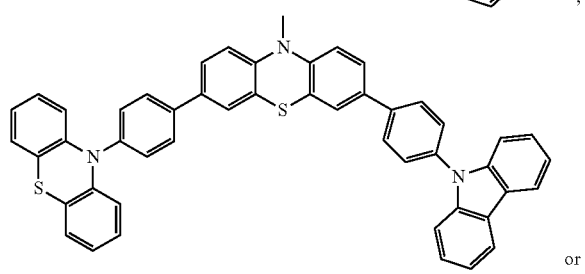

or

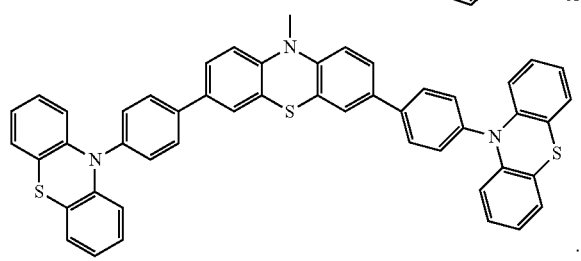

.

7. A organic light emitting diode (OLED) device using a thermally activated delayed fluorescence material, comprising:

a substrate;

a transparent conductive layer, formed on the substrate;

a hole transport layer, formed on the transparent conductive layer;

a light emitting layer, formed on the hole transport layer;

an electron transport layer, formed on the light emitting layer; and a metal layer, formed on the electron transport layer, wherein the light emitting layer comprises a thermally activated delayed fluorescence material comprising a structure formula 1 as

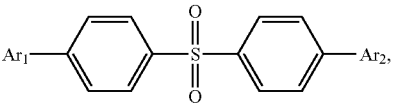

wherein the group $Ar_1$ is identical to or different from the group $Ar_2$, and the group $Ar_1$ and the group $Ar_2$ are selected from the following structural formulas:

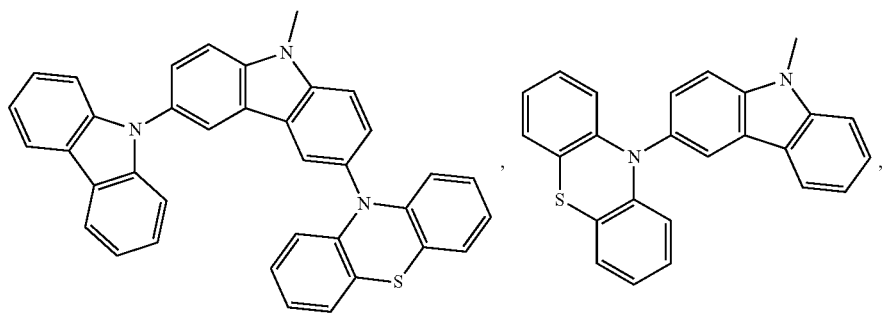

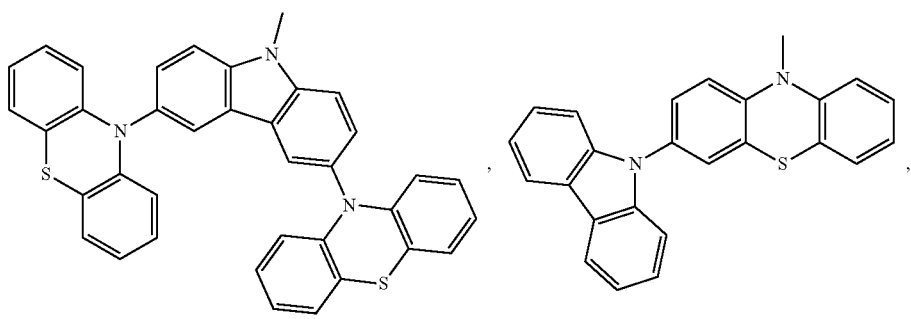

-continued
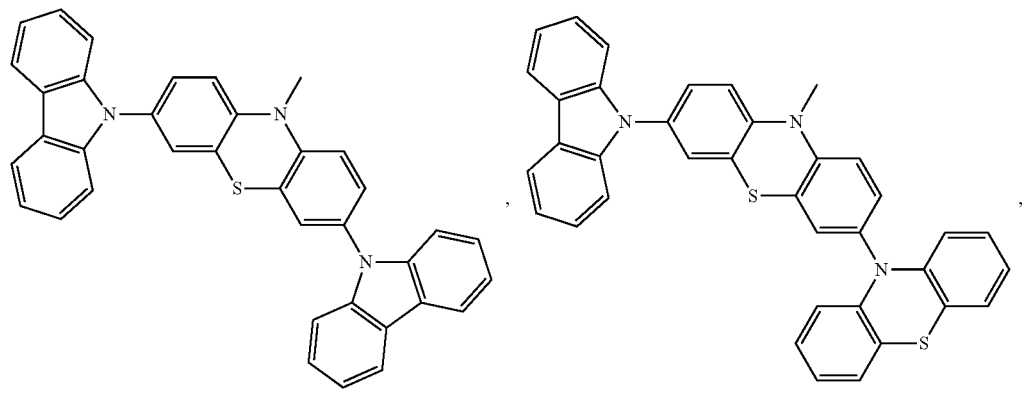
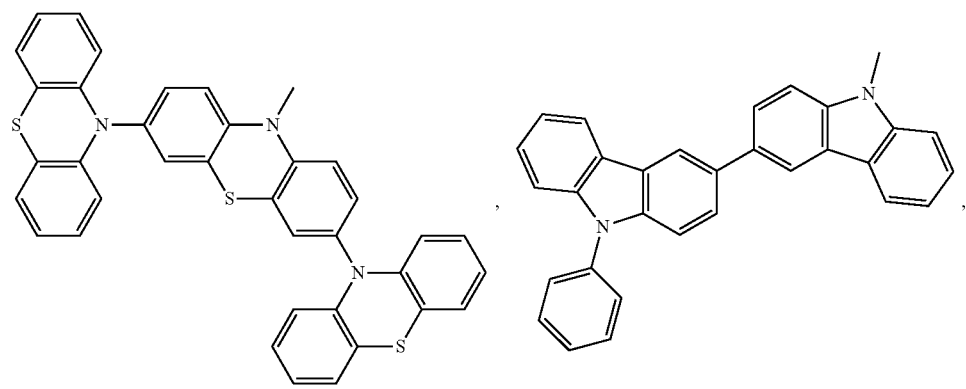
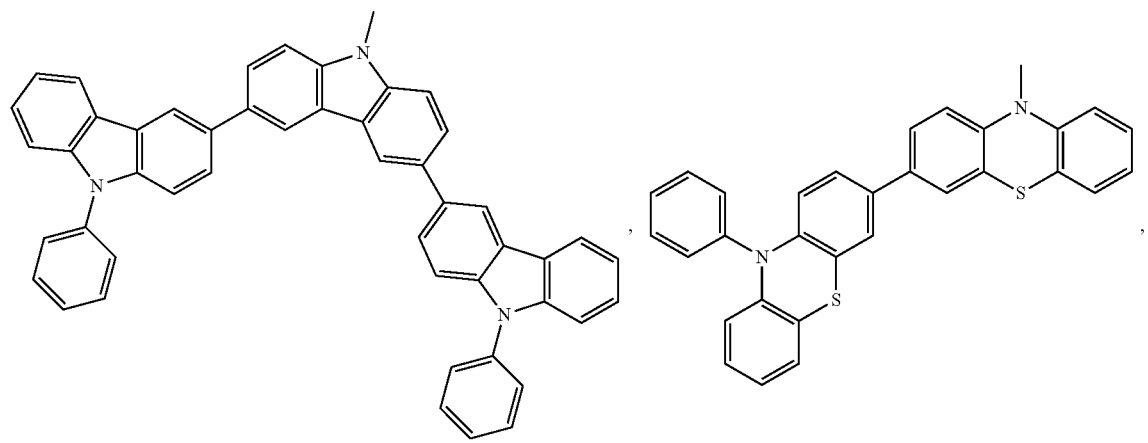
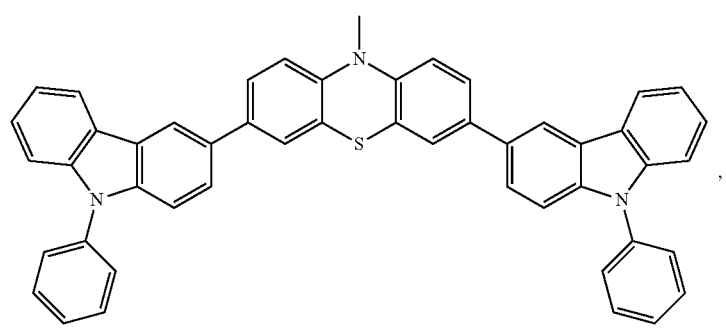

-continued
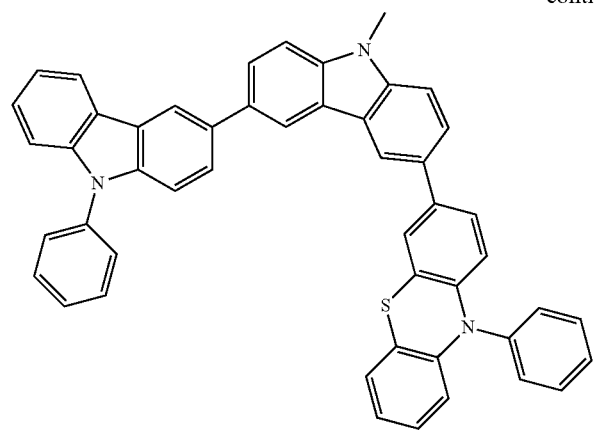
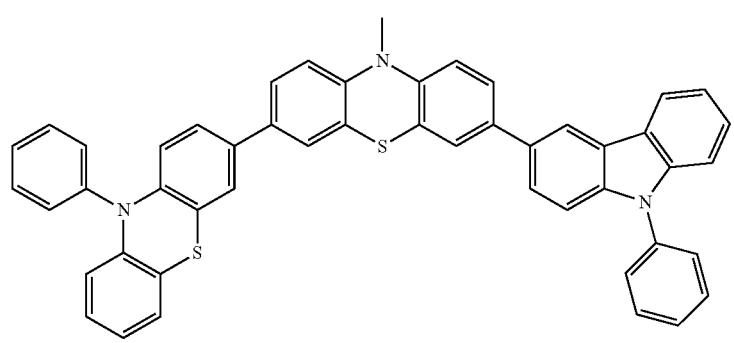
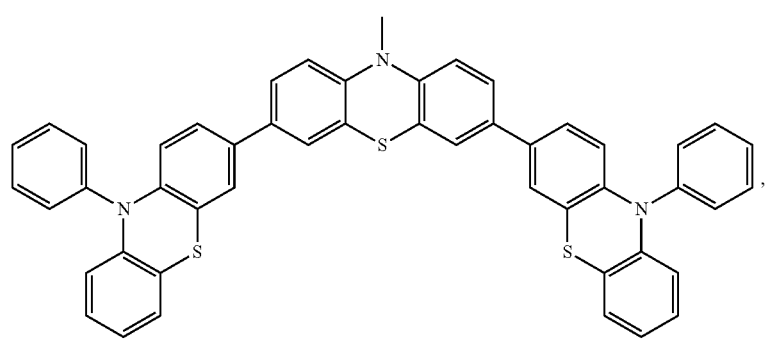
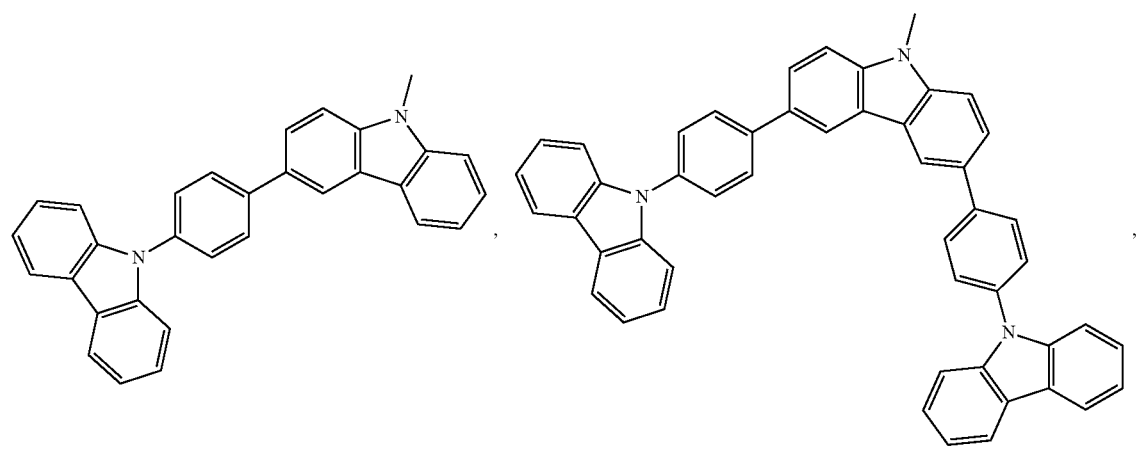

-continued
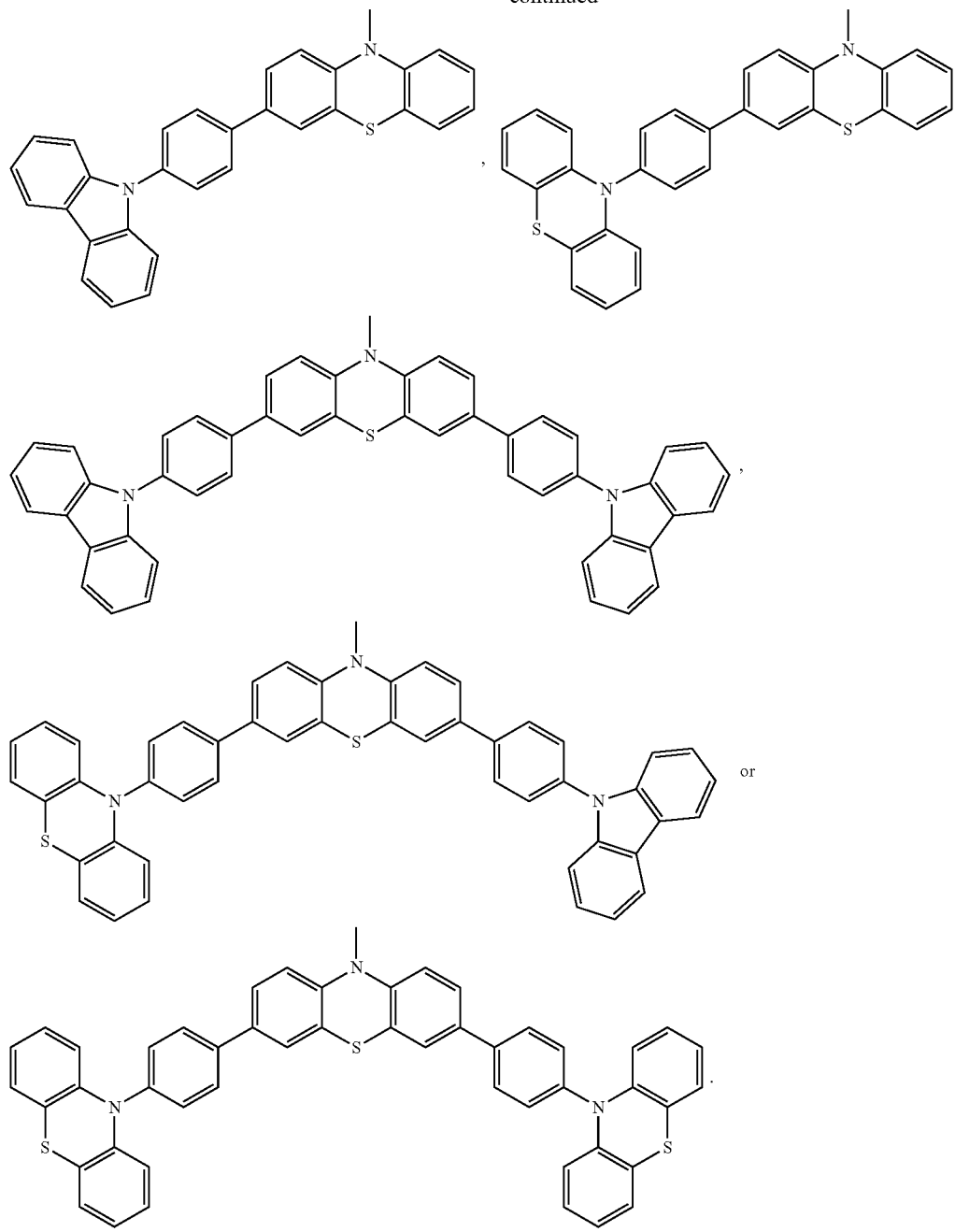
* * * * *